(12) United States Patent
Jones et al.

(10) Patent No.: US 10,478,593 B2
(45) Date of Patent: Nov. 19, 2019

(54) CATHETER HUB WITH REMOVABLE EXTENSIONS

(71) Applicant: The Johns Hopkins University, Baltimore, MD (US)

(72) Inventors: Cameron C. Jones, Pikesville, MD (US); Clifford R. Weiss, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 365 days.

(21) Appl. No.: 15/118,543

(22) PCT Filed: Feb. 17, 2015

(86) PCT No.: PCT/US2015/016216
§ 371 (c)(1),
(2) Date: Aug. 12, 2016

(87) PCT Pub. No.: WO2015/123689
PCT Pub. Date: Aug. 20, 2015

(65) Prior Publication Data
US 2017/0043126 A1    Feb. 16, 2017

Related U.S. Application Data

(60) Provisional application No. 62/043,036, filed on Aug. 28, 2014, provisional application No. 61/940,552, filed on Feb. 17, 2014.

(51) Int. Cl.
*A61M 25/00*   (2006.01)
*A61M 39/04*   (2006.01)
(Continued)

(52) U.S. Cl.
CPC ........ *A61M 25/0097* (2013.01); *A61M 25/02* (2013.01); *A61M 25/0606* (2013.01);
(Continued)

(58) Field of Classification Search
CPC ............... A61M 39/04; A61M 39/045; A61M 39/1011; A61M 39/105; A61M 2039/1072; A61M 2039/1077; A61M 25/0097
See application file for complete search history.

(56) References Cited

U.S. PATENT DOCUMENTS 4,387,879 A   6/1983  Tauschinski
4,417,890 A * 11/1983  Dennehey ............. A61M 39/20
                                                           138/89

(Continued)

OTHER PUBLICATIONS

Written Opinion of the International Searching Authority in corresponding PCT/US2015/016216, dated May 29, 2015.
(Continued)

*Primary Examiner* — Nathan R Price
*Assistant Examiner* — Anh Bui
(74) *Attorney, Agent, or Firm* — Mintz Levin Cohn Ferris Glovsky and Popeo, P.C.; Peter F. Corless

(57) ABSTRACT

In one aspect, the present invention is directed to a multi-lumen catheter with self-sealing hub and an attachable extension assembly. In a preferred aspect, the present invention can allows removal of the external fluid connections of an elongated percutaneous medical article, such as a catheter or cannula. The percutaneous medical article suitably contains a distal septum that prevents fluid movement within the intraluminal space of the percutaneous medical article, when the fluid connections are removed. A single-use, disposable extension set of one or more single lumen lines with associated clamp and cap is attached for intraluminal access and removed following clinical use. Retaining the catheter transition allows the catheter to be secured using methods common to the art.

10 Claims, 42 Drawing Sheets

(51) Int. Cl.
*A61M 39/10* (2006.01)
*A61M 25/02* (2006.01)
*A61M 25/06* (2006.01)

(52) U.S. Cl.
CPC .......... *A61M 39/04* (2013.01); *A61M 39/045* (2013.01); *A61M 39/105* (2013.01); *A61M 39/1011* (2013.01); *A61M 2025/0253* (2013.01); *A61M 2025/0286* (2013.01); *A61M 2039/1016* (2013.01); *A61M 2039/1072* (2013.01); *A61M 2039/1077* (2013.01)

(56) References Cited

U.S. PATENT DOCUMENTS

| | | | |
|---|---|---|---|
| 2003/0088213 A1 | 5/2003 | Schweikert et al. | |
| 2005/0049555 A1 | 3/2005 | Moorehead et al. | |
| 2005/0256460 A1 | 11/2005 | Rome et al. | |
| 2005/0256461 A1* | 11/2005 | DiFiore | A61M 25/0075 604/247 |

OTHER PUBLICATIONS

International Search Report in corresponding PCT/US2015/016216, dated May 29, 2015.

* cited by examiner

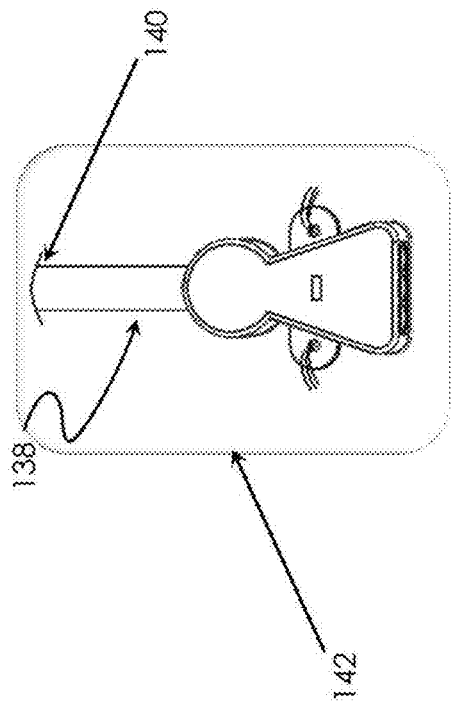
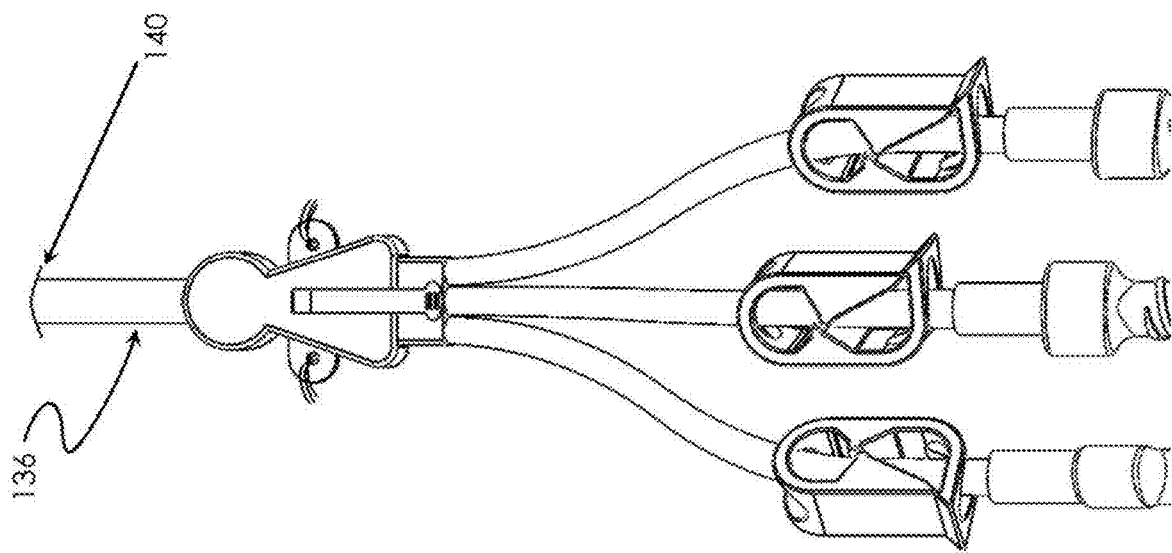
FIG. 13

CATHETER HUB WITH REMOVABLE EXTENSIONS

CROSS REFERENCE TO RELATED APPLICATIONS

The present application is a National Phase of PCT Application No.: PCT/US2015/016216, filed Feb. 17, 2015 and claims priority from U.S. provisional application number 61/940,552 filed Feb. 17, 2014 and U.S. provisional application 62/043,036 filed Aug. 28, 2014, both of which applications are incorporated herein by reference in their entirety.

FIELD OF INVENTION

The present invention relates generally to medical devices. In one preferred aspect, the present invention relates to a self-sealing hub for use with a catheter.

BACKGROUND

Many patients with chronic diseases or who are critically ill require frequent administration of fluids for nutritional or medicinal purposes. These medications are oftentimes delivered through an intravenous catheter such as a central venous catheter (CVC), peripherally inserted central catheter (PICC), and midline catheter, which provide vascular access and can be kept in place for durations lasting several days up to several months. Patients requiring dialysis, for example, may visit the healthcare setting for a few hours each week over a particular rotation, but outside of these dialysis sessions, the catheter is unused but remains indwelling to the patient for future visits.

Modern medical catheters that have a portion of the catheter body extending outside the patient ("percutaneous") consist of an indwelling portion and an external portion that primarily acts as a conduit to the indwelling portion. Many catheters are multi-luminal, where each lumen may serve different functions depending on anatomic location and/or dictated clinical need. External to the patient, the multi-lumen catheter bifurcates into single lumen lines, where the distal ends of said lines consist of a standard medical fitting (e.g., luer) for connecting infusion lines or various medical equipment, and a clamp to prevent fluid movement and air embolism when the catheter is not being accessed. The site of bifurcation is often called the "hub" or "transition" and is traditionally a molded stock connecting the indwelling catheter to the external extension(s), residing immediately adjacent to the insertion site. The intravascular portion of the catheter usually is rich in antimicrobial technologies and has been optimized for fluid dynamic needs, but the hub and extensions, lying external to the patient, generally do not have as rigorous demands on biocompatibility and fluid dynamic function, acting primarily as a conduit for the passage of fluids.

Following placement of the intravascular catheter, it is often necessary to secure the catheter to the patient when used for extended periods of time to prevent axial displacement of the catheter with regards to its anatomical position. Securement of the catheter is generally accomplished by one of three means, which all involve the catheter hub: suturing the catheter hub to the patient's skin through eyelets in the wings extending from the molded hub; applying tape in a crisscross fashion over the catheter hub thereby securing the hub to the patient's skin; or placing the hub in a semi-flexible securement device which is held to the patient's skin by an adhesive base. The securement methods prevent axial movement of the catheter and resist snagging or tugging of external extensions with environmental articles.

Medical catheters are manufactured using polymeric compounds such as silicone, polyethylene, polyurethane, and polytetrafluoroethylene to increase biocompatibility and longevity of use. Despite precautions, catheter-related infections are a frequent and growing concern, having significant consequences to patient morbidity and mortality, and greatly taxing to healthcare resources. Infections stem from bacterial adsorption on the catheter surface, giving way to a prolific growth of a highly antibiotic-resistant community of cells called biofilm. The predominant sources of bacteria that colonize on intravascular catheters arise external to the patient, either through contamination of the intraluminal surface due to non-sterile catheter access (i.e., incomplete disinfection prior to line access) or along the extraluminal surface from microbial egress through the insertion site, facilitated by pistoning (back-and-forth movement of the catheter). Every time these central lines are handled pose a potential risk for contamination.

The long-hanging catheter extensions can cause abrasions to patient skin, are uncomfortable, and are particularly prone to contamination from the patient's daily activities. The extensions may become tangled in clothing or other articles that cause minute axial movement, where such movement can introduce pathogens at the skin surface through back-and-forth motions. In addition, the distal ends of the catheters, where caps and other barriers are attached, are easily dirtied, which can pose a risk to contaminating the sterile catheter lumen during clinical access. Moreover, such caps and barriers can be removed outside the clinical setting and reattached without proper cleaning; in such cases, bacteria colonize under the cap and are introduced to the entire intraluminal space and patient's bloodstream during the next clinical use. Furthermore, these extensions can sometimes break: inexpensive clamps are snapped, tubing becomes kinked, and so forth; and such event requires surgical intervention to replace the entire catheter.

Most protocols of prevention and treatment secondary to the imbued biocompatibility of the catheter involve daily cleaning of insertion site and locking the intraluminal space with potent antibiotics or anti-thrombogenic agents. In addition to the many antimicrobial coatings and novel characteristics to the catheter surface, all of these technologies address the complication of infection after contamination has already occurred, that is, by acting as a defense against a present contaminant.

It would therefore be advantageous to provide a self-sealing hub for use with a catheter that allows attachment and removal of various extensions, reduces the total surface area of the extravascular portion of the catheter for bacterial contamination, removes the portion that is most often the source of an infection's origin, facilitates better placement of insertion-site dressing, and removes the region prone to snagging, irritation, and other problems associated with dangling catheter extensions.

SUMMARY

We now provide new catheter systems and methods for use of such systems.

In one preferred aspect, a catheter is provided that comprises a) a catheter unit; and b) an extension tube assembly that is releasably attached to the catheter unit. In a preferred use, the extension tube assembly can be released from the catheter while the catheter unit is affixed to a patient.

More particularly, in a preferred aspect, a catheter is provided that includes a catheter unit that comprises a hub having an outer housing defining a proximal end and a distal end. The distal end of the outer housing defines an opening into an inner space defined by the outer housing, and is disposed within the inner space is a distal connector. Additionally, the proximal end of the housing defines a proximal connector for coupling to an intravenous catheter tube. The catheter also includes an extension tube assembly that is releasably attached to the connector and can be released from the catheter while the catheter unit is affixed to a patient. The extension tube assembly is suitably releasably engaged to the catheter unit by any of a variety of systems, including e.g. a mechanical or magnetic system. For instance, the extension tube assembly may include a releasably locking key-type connector for coupling the extension tube to the catheter unit.

In an additional aspect, a catheter is provided that includes a hub having an outer housing defining a proximal end and a distal end. The distal end of the outer housing defines an opening into an inner space defined by the outer housing. A distal connector is disposed within the inner space. The proximal end of the housing defines a proximal connector for coupling to an intravenous catheter tube. The catheter also includes a self-sealing septum disposed within the opening defined by the distal end of the outer housing, such that the self-sealing septum forms a barrier for the distal connector. Additionally, the catheter includes an extension tube assembly. The extension tube assembly includes an extension tube and a locking key-type connector for coupling the extension tube to the distal connector through the self-sealing septum.

In accordance with an aspect of the present invention, the catheter includes a locking key-type cover for covering the opening and the septum when the catheter is not in use. The locking key-type cover suitably further comprises plugged luer channels. The extension tube further includes a number of extension tubes in a range of e.g. 1-4 extension tubes. The self-sealing septum further includes slits in order to allow the connection of the extension tube assembly. The catheter includes a luer. The luer is separated into a plunger and a luer taper. The plunger includes threading. The self-sealing septum is reset using a slider or elastic band mechanism. The catheter can also include an integrated catheter connector with a septa/um and a clamp. A secondary clamp that enables replacement of the extension tube assembly can also be included. The intravenous catheter tube includes a single lumen or multiple lumens.

In accordance with another aspect of the present invention, the present invention provides a method for releasably attaching e.g. input lines to a catheter assembly. The method suitably includes affixing a catheter to a surface (e.g. skin) of a patient for instance by either a suturing method or using an adhesive. The catheter includes a catheter unit and an extension tube assembly that can be removed from the catheter as desired while the patient is not being treated. The same extension tube assembly then can be suitably re-attached to the catheter during treatment of the patient (e.g. to introduce drug to the patient), or another extension tube assembly can be attached to the catheter unit. Accordingly, the entire catheter is not required to be removed from patient, thus eliminating the potential increase medical risks to the patient. The extension tube assembly is suitably attached to the catheter by any of a variety of arrangement including e.g. a mechanical engagement of the extension tube assembly and the catheter unit. Alternatively, the extension tube assembly is attached by a magnetic engagement of the extension tube assembly and the catheter unit, thus preventing disturbance to the portion of the catheter within the patient.

Notably, the present invention is not limited to the combination of catheter elements as listed above and can be assembled in any combination of the elements as described herein.

Other aspects of the invention are disclosed infra.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIG. 13 illustrates a perspective view of a traditional indwelling multi-lumen catheter (left) alongside a catheter transition with removable extensions (right) according to an embodiment of the present invention.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

In one aspect, the present invention is directed to a multi-lumen catheter with a self-sealing hub and an attachable extension assembly. More particularly, the present invention is directed to a technology that allows removal of the external fluid connections of an elongated percutaneous medical article, such as a catheter or cannula. The present invention contains a distal septum that prevents fluid movement within the intraluminal space of the percutaneous medical article, when the fluid connections are removed. A single-use, disposable extension set of one or more single lumen lines with associated clamp and connector is attached for intraluminal access and removed following clinical use. Retaining the catheter transition allows the catheter to be secured using methods common to the art.

Figure 1:
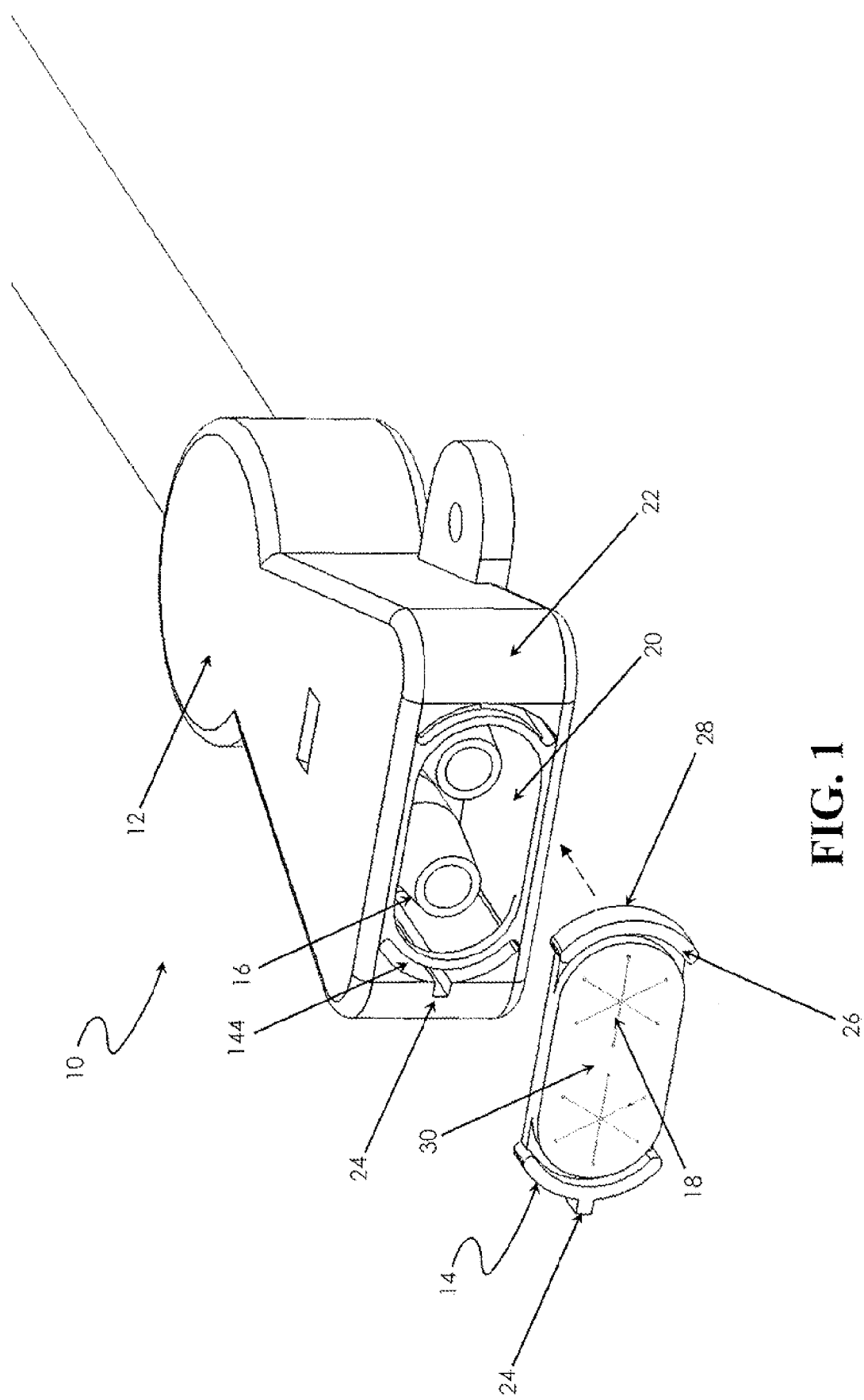
FIG. 1 illustrates an exploded view of a self-sealing catheter according to an embodiment of the present invention.

FIG. 1 illustrates an exploded view of a self-sealing catheter according to an embodiment of the present invention. As illustrated in FIG. 1, a self-sealing catheter assembly 10 includes a hub 12 and an elastic septum 14. When assembled into the self-sealing catheter assembly 10, the elastic septum 14 is positioned immediately adjacent to internal single lumen fittings 16, within the housing of the hub 12. The elastic septum 14 further includes one or more slits 18 that seal the intraluminal fittings 16 in a closed state, and allow fluid access to internal lumen fittings 16 in an open state.

As noted with respect to FIG. 1, the catheter hub 12 contains an inner region 20 where one or more lumens of the intravascular catheter bifurcate into single lumen fittings 16. The single lumen fittings 16 are of a generally frustoconical form. However, the single lumen fittings 16 can take any suitable form known to one of skill in the art. The elastic septum 14 is disposed between the inner region 20 and an outer region 22. The elastic septum 14 may take the form of a polarized fitting 24 between the inner region 20 and the outer region 22. The larger outer region 22 encompasses both the inner region 20 and elastic septum 14, includes a plurality of openings in addition to common securement features such as wings and eyelets which are attached to the patient by securement means known to those of skill in the art. A single opening can expose an area of the septum that seals the individual connection sites. Additional openings exist surrounding the entire distal portion of the catheter hub which act as both alignment mechanisms for the attachable extension set and, in a preferred embodiment, allow the alignment pins of the attachable extension set to open the septum in a manner that enables a sterile connection.

Further, with respect to FIG. 1, the elastic septum 14 includes an inner surface 28 and an outer surface 30 and is a single, flexible, synthetic polymer having high elasticity and preformed shape, including one or more slits 18. The septum 14 includes one or more tabs 26, having a compressibility equal to or less than that of the septum material, that rest within an open channel 144 between the larger outer region 22 and inner region 20. Attachment of the alignment mechanisms of the extension set engage with the tabs 26 which are pressed through the channels 144, thereby stretching the septum 14 in a preferred direction, whereby, such elongation widens the slit 18 in the septum 14 revealing open fittings 16 of the inner hub region 20. With the septum 14 being contained within the outer region 22 and elongation of the septum 14 is guided along an inner track 144, the inner surface 28 of the septum 14 remains sterile. The tabs 26 of the preferred embodiment, seal inner channels 144 disposed between the outer and inner regions when no extension set is attached.

Figure 2:
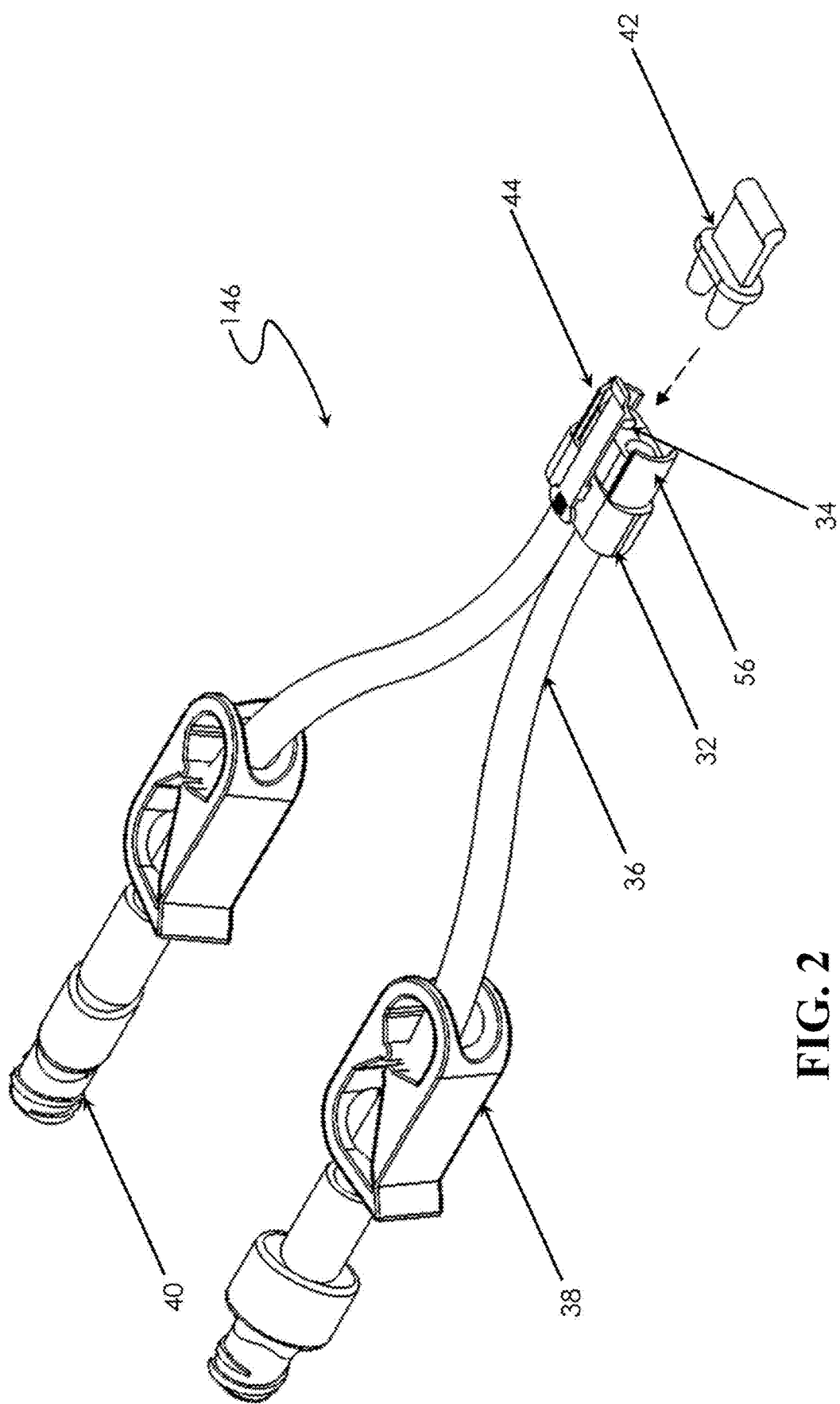
FIG. 2 illustrates an exploded view of a removable extension set with protective cap used in conjunction with a self-sealing catheter according to an embodiment of the present invention.

FIG. 2 illustrates an exploded view of a removable extension set with protective cap used in conjunction with a self-sealing catheter according to an embodiment of the present invention. As illustrated in FIG. 2, the disposable extension set 146 includes a key-type connector 32 having a molded form with individual lumen fittings 34, and additional members common to the distal portion of traditional percutaneous catheters, including: extension tubing 36, clamps 38, and luer fittings 40. The extension set 146 is intended to be a disposable single-use system, individually packaged with a fluid prime. Prior to attachment to the self-sealing multi-lumen catheter, a small tab 42 which seals a proximal end 44 of the key-type connector 32 is removed.

Further with respect to the disposable extension set 146, as illustrated in FIG. 2, one or more single lumen extensions tubes 36 converge to a common connector 32 that engages with matching features of the self-sealing catheter hub. In an embodiment according to the present invention, each single lumen extension tube 36 corresponds to a single frustoconical form which mates with a matching form in the catheter hub. The male end fitting may be on either the extension connector or on the catheter hub, or may consist of combinations thereof for one-way connectivity. The extension connector and hub assembly may alternatively utilize an asymmetric arrangement of the alignment members 56 or incorporate a particular shape feature to impart a particular polarization or orientation.

In an embodiment according to the present invention, the alignment members of the extension connector extend longer than any other protruding members in order to engage with the tabs of the septum, thereby revealing the inner region of the catheter hub, as the extension fittings engage with the catheter hub. In this way, the septum is opened and the frustoconical members are connected in an aseptic manner. This key-type connection additionally minimizes the potential for misuse of the vascular access device.

Figure 3:
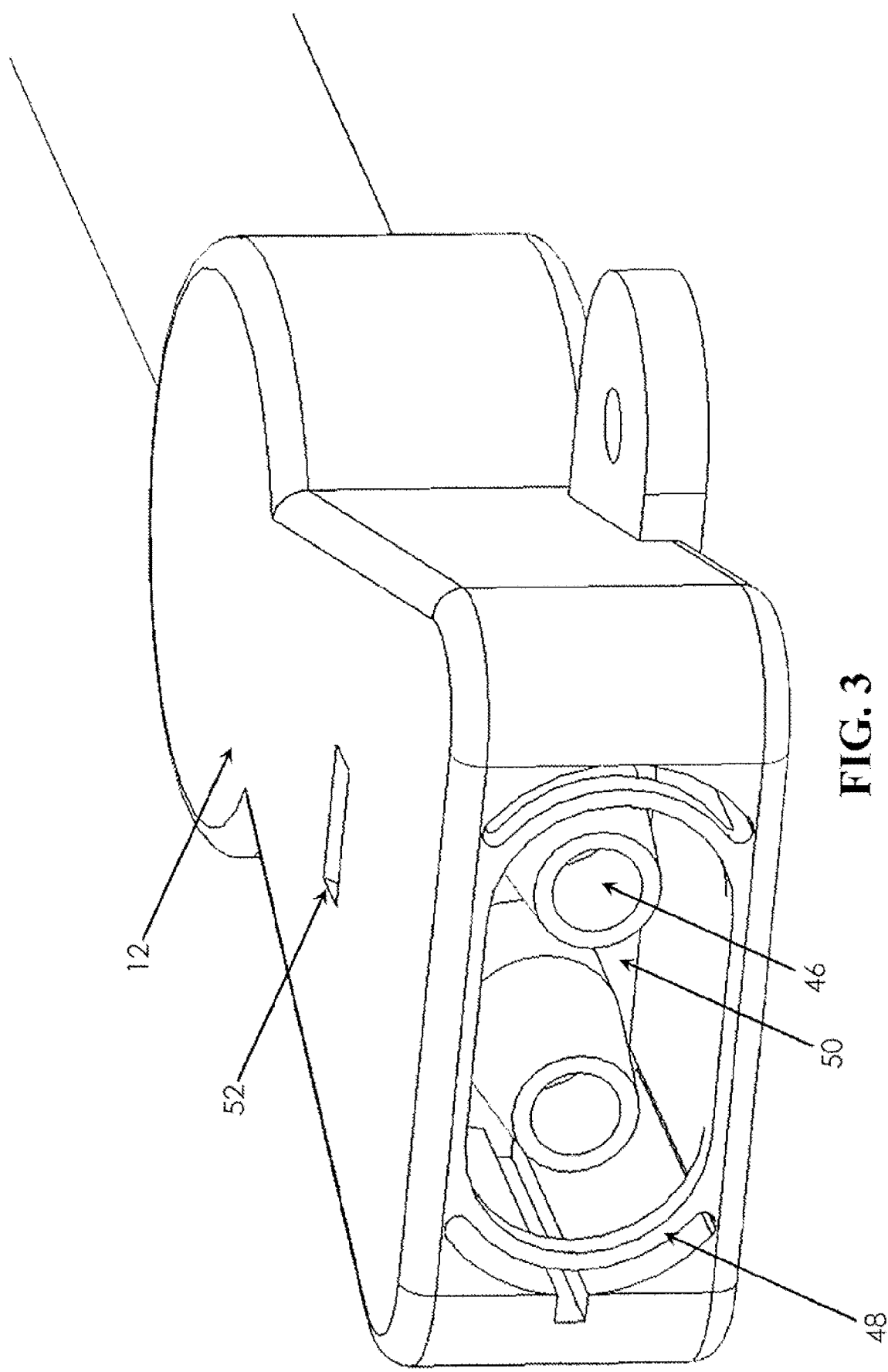
FIG. 3 illustrates a perspective view of a distal end of a catheter transition, according to an embodiment of the present invention.

FIG. 3 illustrates a perspective view of a distal end of a catheter transition, according to an embodiment of the present invention. In an embodiment according to the present invention, single lumen fittings 46, in the form of frustoconical bosses are internal to the catheter hub 12 wherein the multi-lumen catheter bifurcates into individual lumen fittings 46. The elastic septum (not illustrated) is disposed between the distal portions of the lumen fittings 46 and is wholly contained within the outer edge of the catheter transition, having a retaining barrier 48 to prevent the septum from being removed after assembly. The septum is displaced towards a back wall 50, in the direction of the insertion site, by the attachment of a removable extension set, whereby the lumen fittings are uncovered. The removable extensions have one or more alignment members which engage with matching alignment regions of the catheter transition, having a particular polarization, which displace the septum towards the back wall 50, providing fluid access to the single lumen fittings. The removable extensions are temporarily secured to the catheter hub by a locking mechanism 52 disposed on the outer surface of the catheter hub 12.

Figure 4:
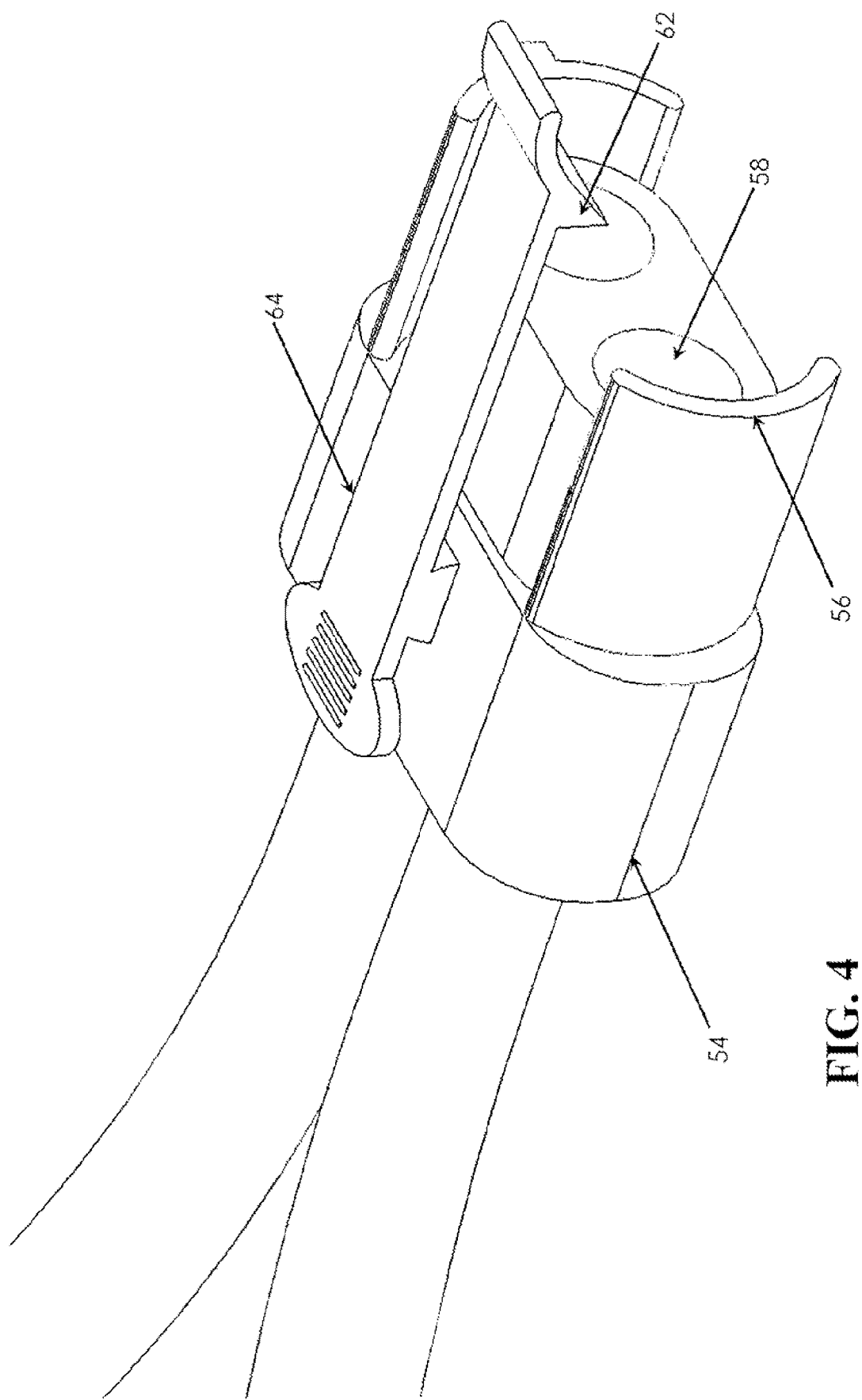
FIG. 4 illustrates a perspective view of a key-type fitting with recessed frustoconical regions which engage with matching features of a catheter transition, according to an embodiment of the present invention.

FIG. 4 illustrates a perspective view of a key-type fitting with recessed frustoconical regions 58 which engage with matching features of a catheter transition, according to an embodiment of the present invention. In an embodiment according to the present invention, a key-type connector 54 includes shaped members having a matching orientation with the catheter hub 12. The alignment members 56, which in a preferred embodiment also function to displace the resealable septum, guide the matching frustoconical region 58 towards the respective region on the catheter hub. Once the extension connector is fully seated against the catheter hub, the frustoconical members share a common surface, thereby creating a fluid-tight junction. The alignment members 56 extend further than the lumen fittings in order to displace the septum, which provides access to the lumens within the catheter hub, prior to engaging the frustoconical fittings. In this way, the fittings 58 of the key-type connector do not touch the resealable septum, preserving a sterile connection with the matching indwelling lumen fittings. A locking mechanism, such as a locking tab with releasing member 62 extending from a cantilevered arm 64 temporarily secures the removable extension assembly to the catheter hub during lumen access.

Figure 5:
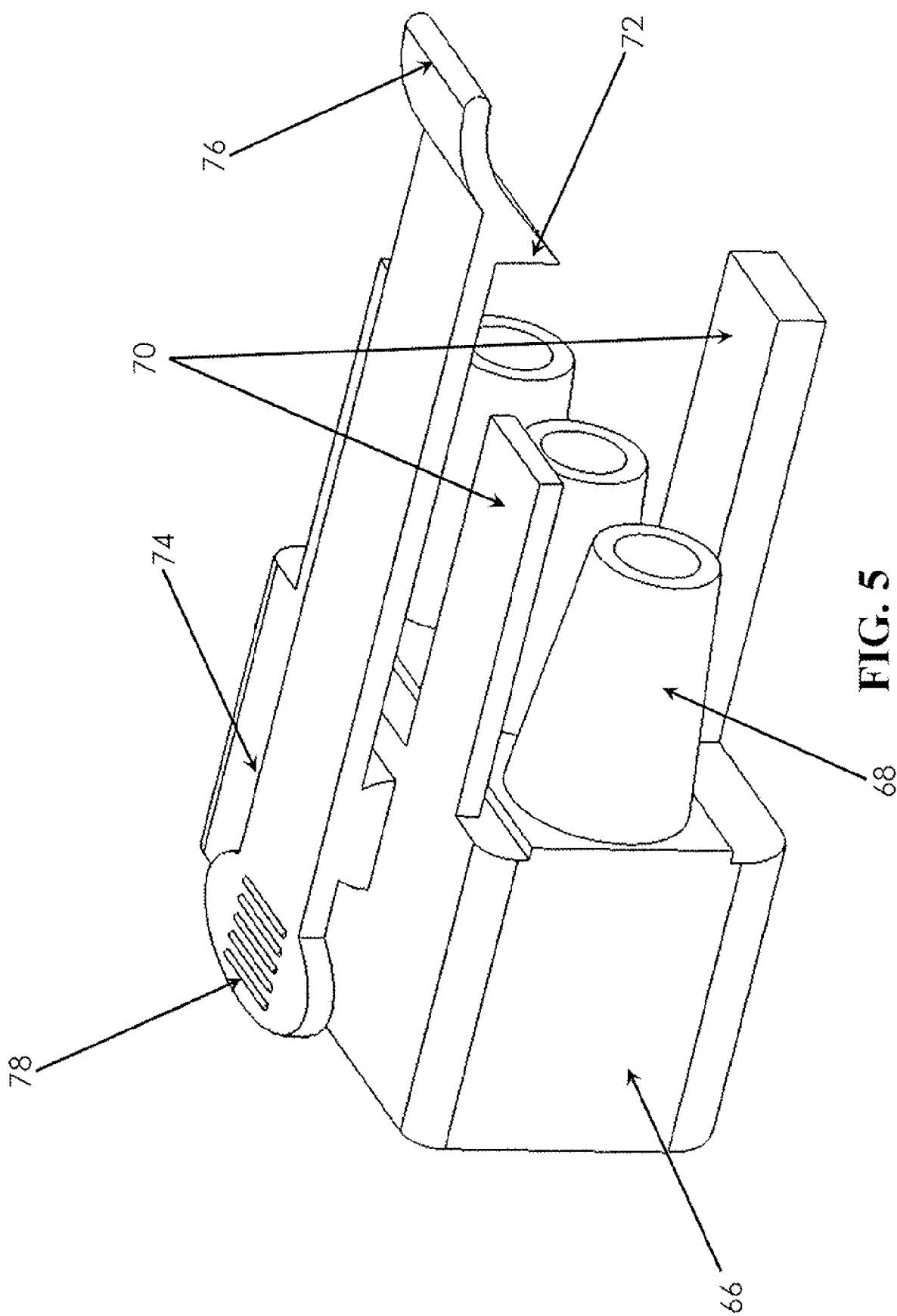
FIG. 5 illustrates a perspective view of a key-type fitting with frustoconical bosses which engage with matching features of a catheter transition, according to an embodiment of the present invention.

FIG. 5 illustrates a perspective view of a key-type fitting with frustoconical bosses which engage with matching features of a catheter transition, according to an embodiment of the present invention. The key-type connector 66, illustrated in FIG. 5 includes frustoconical bosses 68 that engage with matching recesses within a catheter hub. The connector 66 has an asymmetrical arrangement of alignment members 70 to ensure one-way connectivity. Temporary securement of the extension set with the catheter hub is accomplished by a locking mechanism such as a locking tab 72 located on a cantilevered beam 74 and having a releasing means such as a pull tab 76 or a push region 78.

Figure 6:
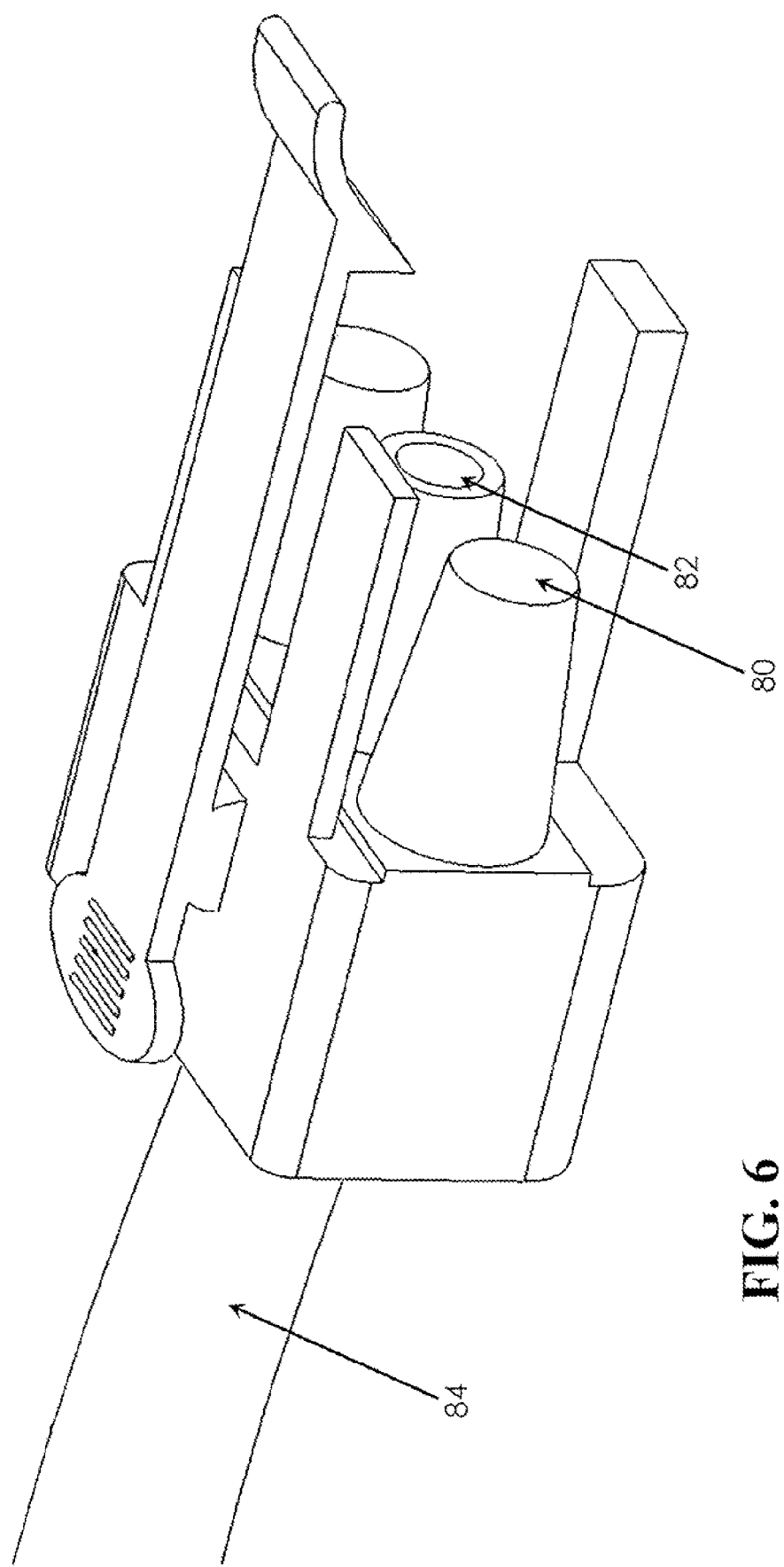
FIG. 6 illustrates a perspective view of a universal key-type fitting for a given multi-lumen catheter that is used when fewer single lumen extensions of a disposable extension set are needed than a number of lumens of a multi-lumen catheter, according to an embodiment of the present invention.

FIG. 6 illustrates a perspective view of a universal key-type fitting for a given multi-lumen catheter that is used when fewer single lumen extensions of a disposable extension set are needed than a number of lumens of a multi-lumen catheter, according to an embodiment of the present invention. Often not all lumens of a multi-lumen catheter are required for a particular clinical need, such as for common blood draws. The key-type connector for a particular multi-lumen catheter may be of universal fit, where one or more frustoconical members are non-patent 80, with one patent member 82 for every single lumen extension 84 distal to the molded key-type connector.

Figure 7:
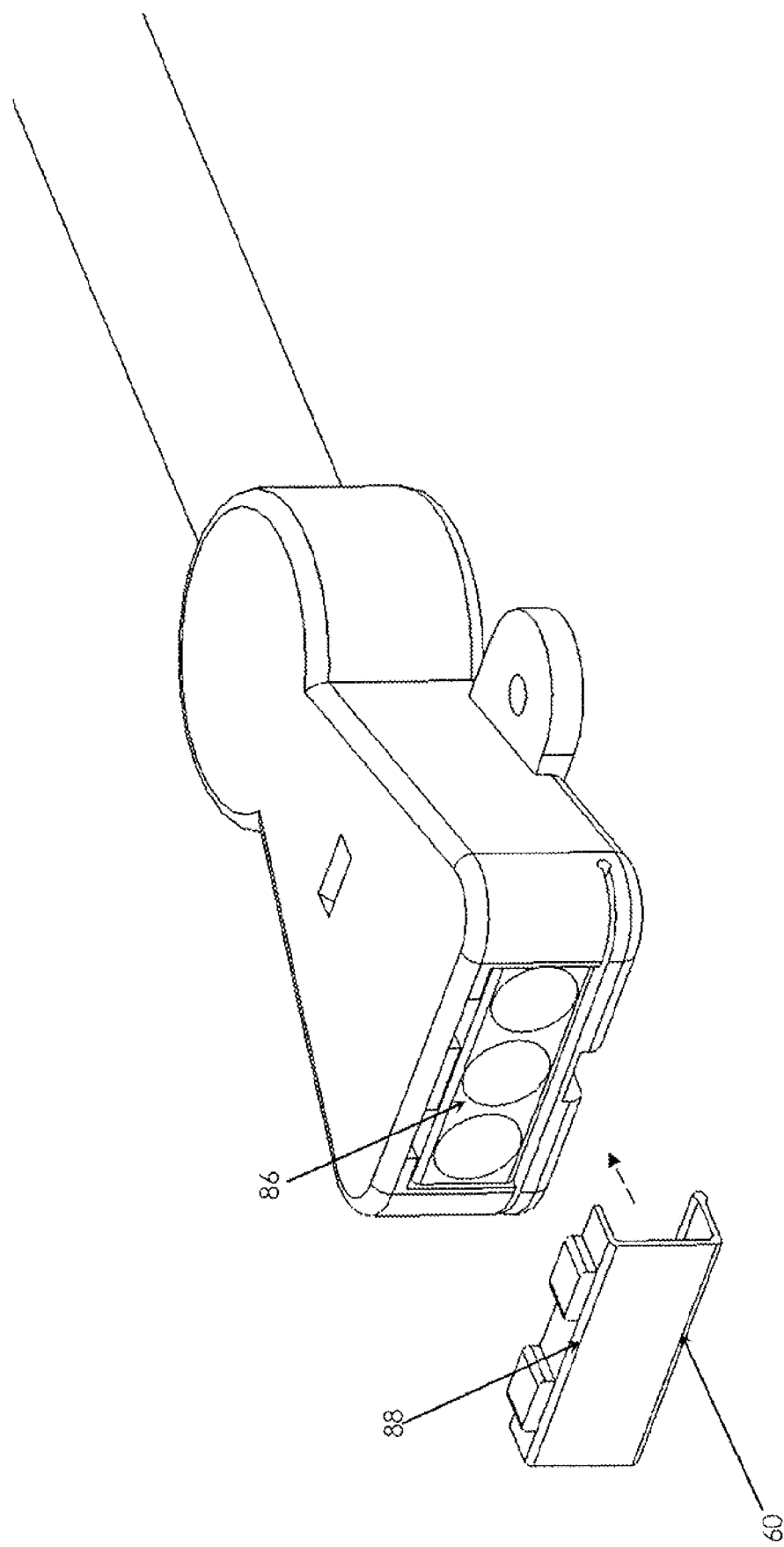
FIG. 7 illustrates a perspective view of an exemplary catheter transition having internal frustoconical recesses for receiving frustoconical bosses of matching shape, according to an embodiment of the present invention.

FIG. 7 illustrates a perspective view of an exemplary catheter transition having internal frustoconical recesses for receiving frustoconical bosses of matching shape, according to an embodiment of the present invention. In this embodiment, the catheter hub is a triple-lumen bifurcation 86 having recessed frustoconical lumen fittings with a resealable septum 88 (shown in exploded view) affixed at one side within the catheter hub and where said septum has a single resealable slit 60.

Figure 8:
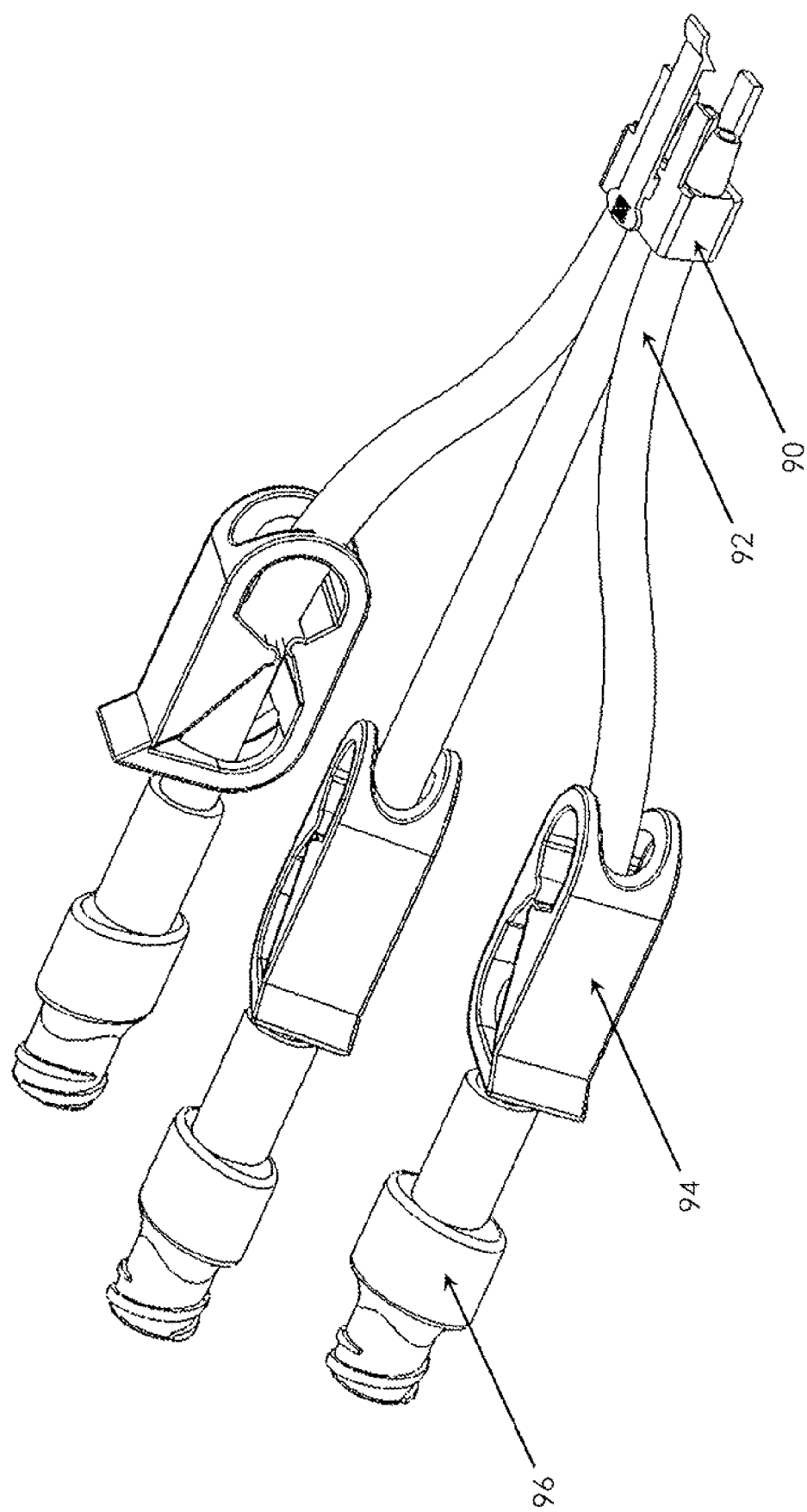
FIG. 8 illustrates a perspective view of a triple-lumen extension set, according to an embodiment of the present invention.

FIG. 8 illustrates a perspective view of a triple-lumen extension set, according to an embodiment of the present invention. The extension set illustrated in FIG. 8 includes a molded key-type connector 90 with three frustoconical bosses, having three single lumen extensions 92 with respective clamps 94 and luer fittings 96.

Figure 9:
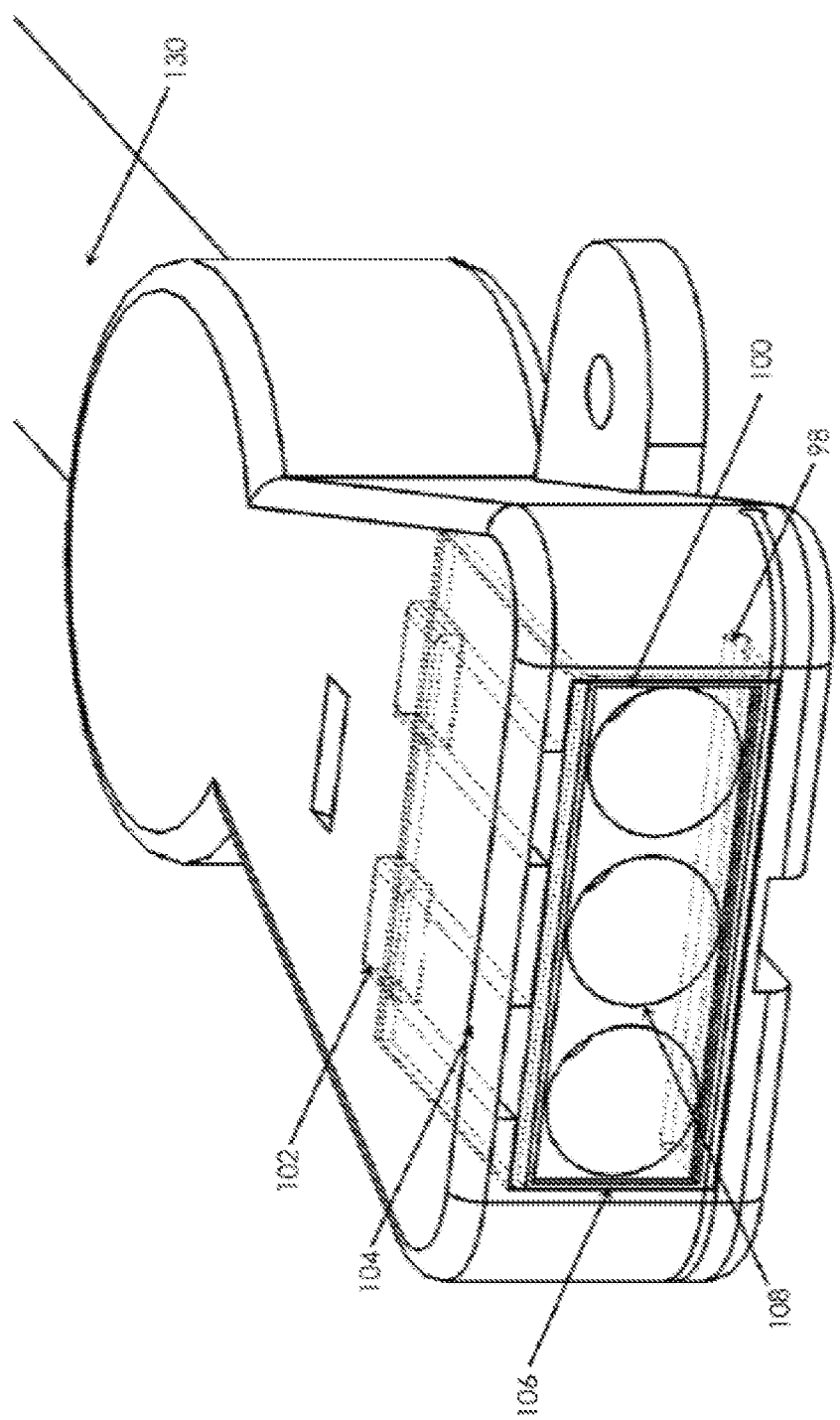
FIG. 9 illustrates a perspective view of an open state of a resealable septum on a multi-lumen catheter transition having frustoconical recesses for fluid lumen coupling and a septum fixed at one side, being elongated by the displacement of tabbed members on an opposite side, according to an embodiment of the present invention.

FIG. 9 illustrates a perspective view of an open state of a resealable septum on a multi-lumen catheter transition having frustoconical recesses for fluid lumen coupling and a septum fixed at one side, being elongated by the displacement of tabbed members on an opposite side, according to an embodiment of the present invention. The multi-lumen catheter transition in FIG. 9 illustrates the open state of the resealable septum. The resealable elastic septum is affixed by its base 98 to the catheter transition. Elongation of the septum 100 is achieved by directing tabs 102 along an internal channel 104 by the attachment of the key-type extension connector, which thereby widens the single slit 106 in the resealable septum larger than the opening required for connection of the matching lumen fluid fittings 108. In the closed state, the resealable septum completely seals the lumen fittings 108. Also, during the closed state the tabs 102 are flush with the edge of the catheter transition which prevents debris from entering the internal channel(s) 104. In the closed state, all cavities within the catheter hub are sealed by the elastic septum.

Figure 10:
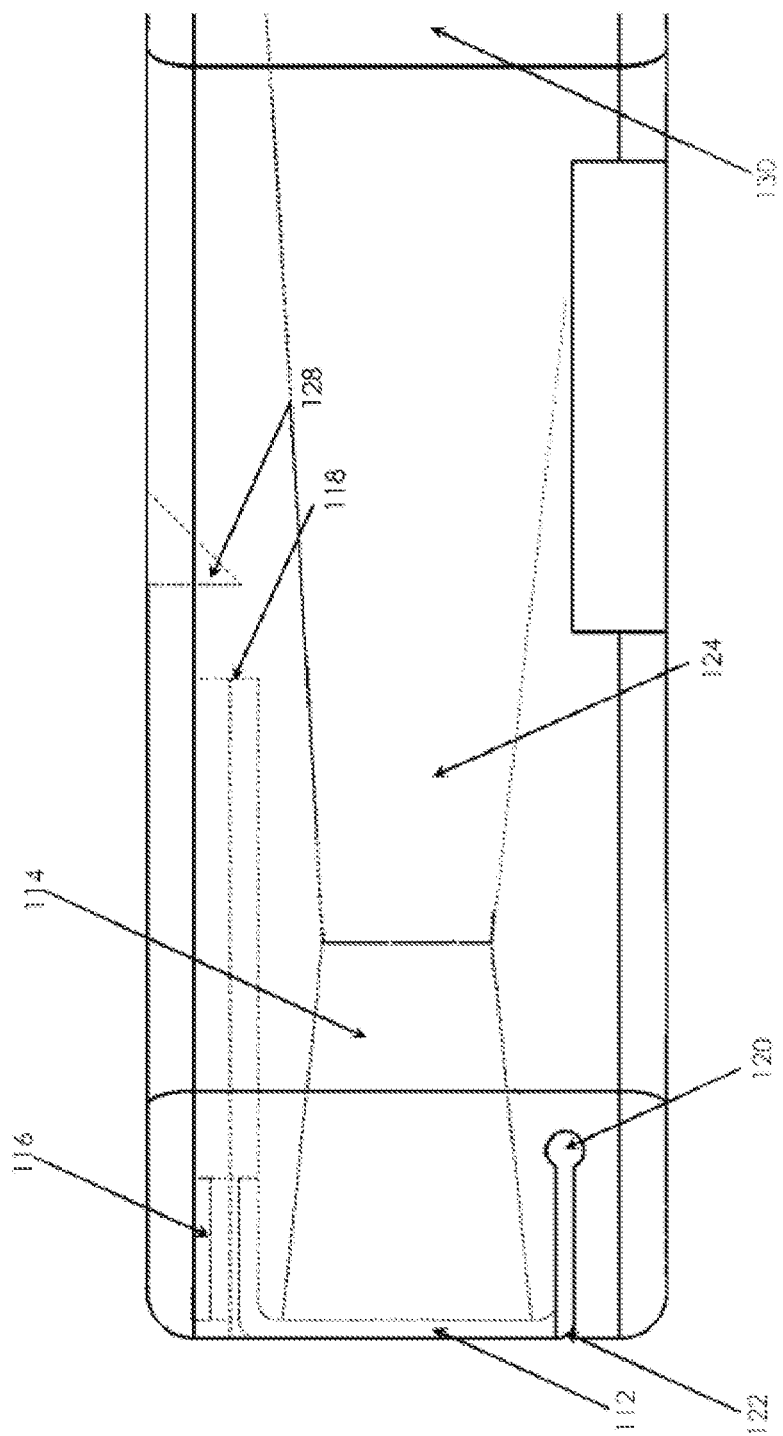
FIG. 10 illustrates a profile view of a closed state of the septum and catheter transition illustrated in FIG. 9.
Figure 11:
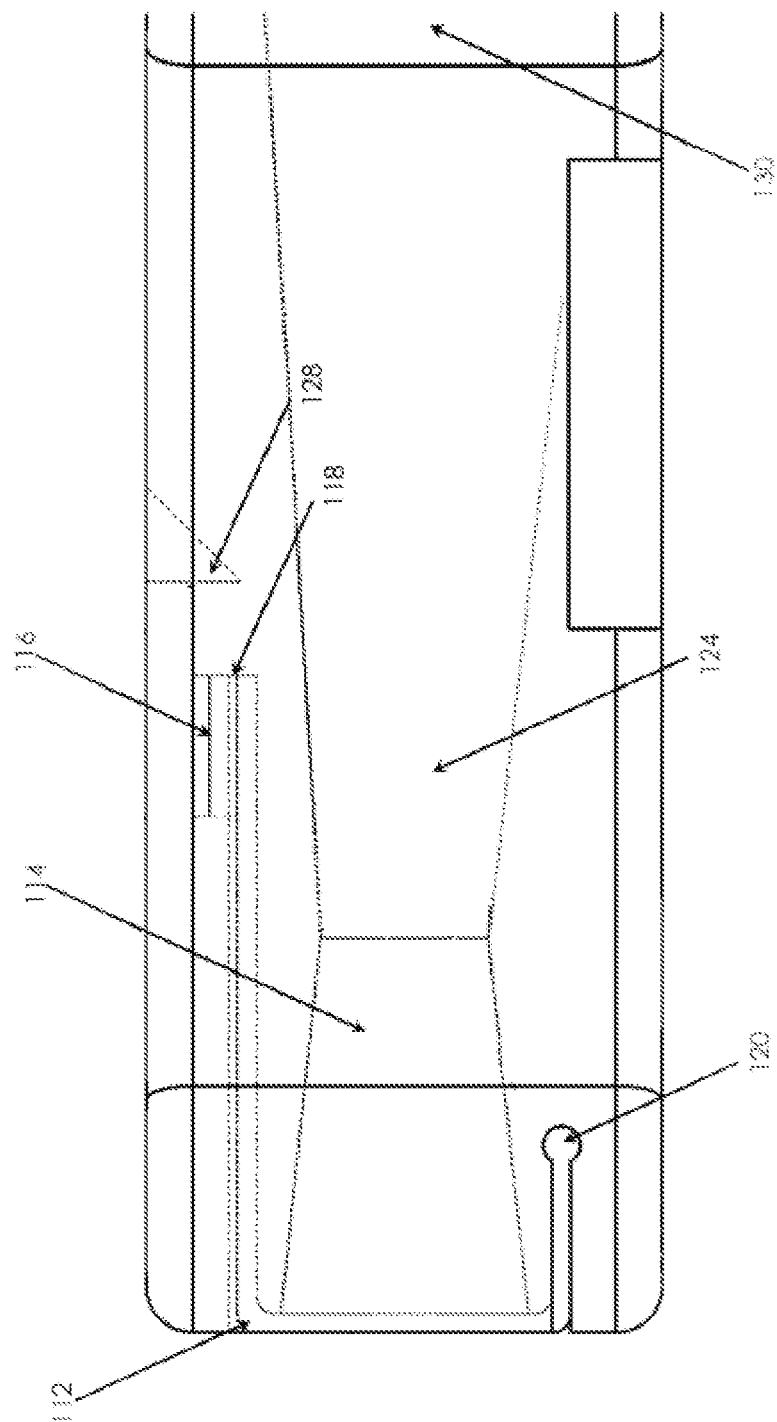
FIG. 11 illustrates a profile view of an open state of the septum and catheter transition of FIG. 10.

FIG. 10 illustrates a profile view of a closed state of the septum and catheter transition illustrated in FIG. 9 and FIG. 11 illustrates a profile view of an open state of the septum and catheter transition of FIG. 10. In the closed state, the septum 112 seals internal fluid fittings 114. Tabs 116 at the top of the septum are at the distal portion of the transition and prevent debris from entering the guide tracks 118 where the septum elongates. Upon attachment of the extension set, the tabs 116 are pushed along the internal track 118 and the septum 112 is maintained at the base 120 such that the slit in the septum 122, which is sealed in the closed state and residing partially contained within the internal catheter transition, widens to allow access to the internal fluid fittings 114. The guide tracks 118 may be straight, or alternatively, contain a shaped feature such as a tapering or boss which retains the tabs. A temporary locking means on the key-type connector engages with a locking region 128 of the catheter transition and maintains a secure connection during use of the extensions. Internal lumens 124 converge within the catheter transition to a single multi-lumen catheter 130. In the open state, of FIG. 11, the septum 112 is now elongated by sliding the tabs 116 along the internal channel 118 following the attachment of the key-type connector.

Figure 12:
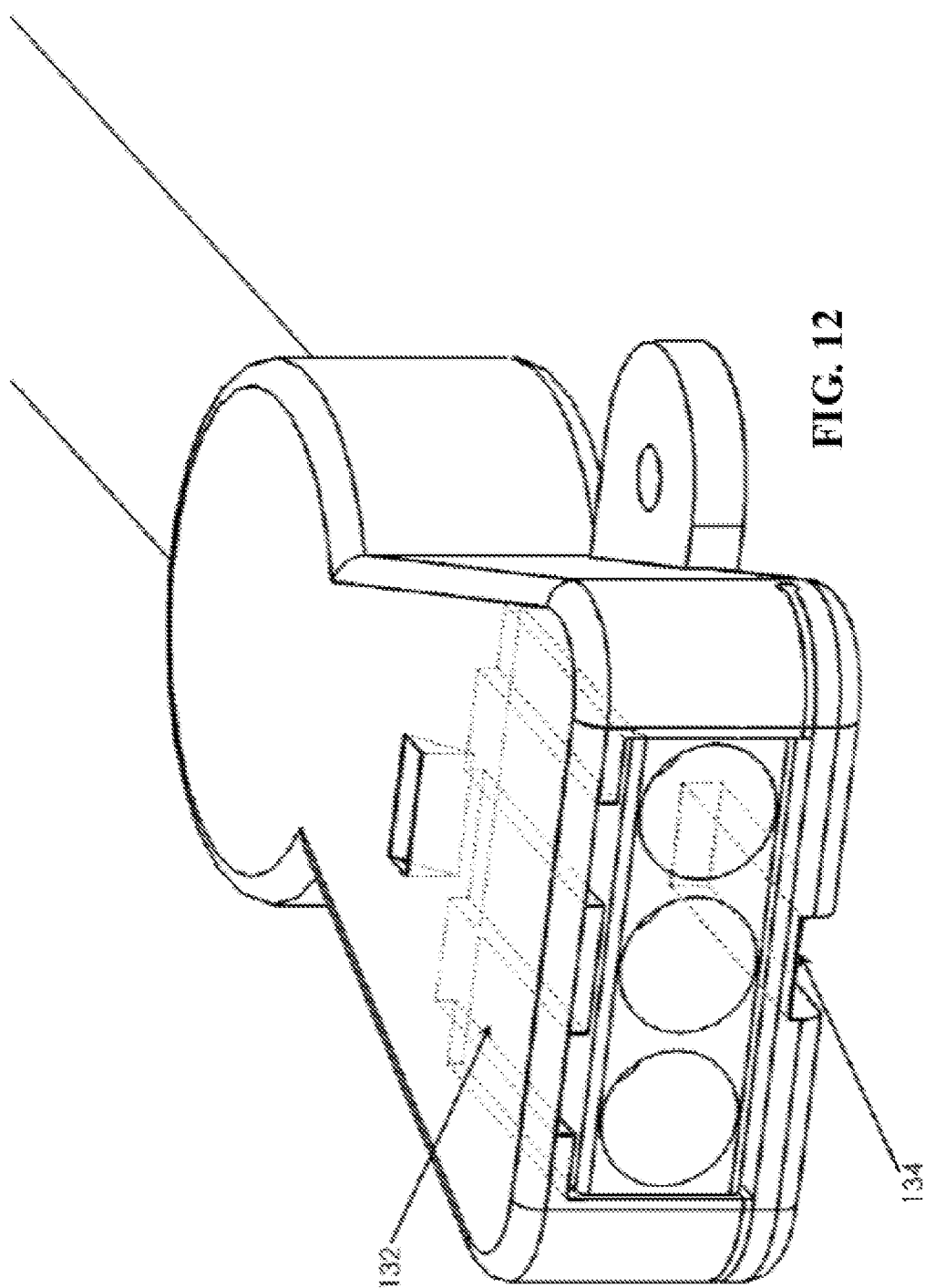
FIG. 12 illustrates a perspective view of a catheter transition and its alignment members, according to an embodiment of the present invention.

FIG. 12 illustrates a perspective view of a catheter transition and its alignment members, according to an embodiment of the present invention. Alignment members may be asymmetrically positioned around the catheter transition, and further, may not all be involved in the process of displacing the septum for opening connections to the intraluminal fittings. In one embodiment, the septum is affixed at the catheter base and opening occurs by displacing tabs at the opposite end, thereby stretching the resealable septum slit wider than the frustoconical members (cf. FIGS. 10 and 11). In said embodiment, a series of alignment members on the key-type connector slide along an internal tract 132 and subsequently also displace the septum tabs, opening the septum for access to lumen fittings. Existing along another portion of the catheter hub are additional channels acting exclusively as alignment guides 134 wherein the septum is not disposed.

FIG. 13 illustrates a perspective view of a traditional indwelling multi-lumen catheter (left) alongside a catheter transition with removable extensions (right) according to an embodiment of the present invention. A modern indwelling percutaneous catheter 136 is shown in FIG. 13. The large surface area of the extensions is easily dirtied and is the principal site of contamination; moreover they are prone to snagging, tugging, and other irritations to the patient. The present invention with removable extensions 138 has lower surface area for contamination and eliminates the problematic extensions. Furthermore, the low-profile design enables the entire external catheter portion, including the insertion site 140 to be protected by a sterile adhesive bandage 142.

Figure 14:
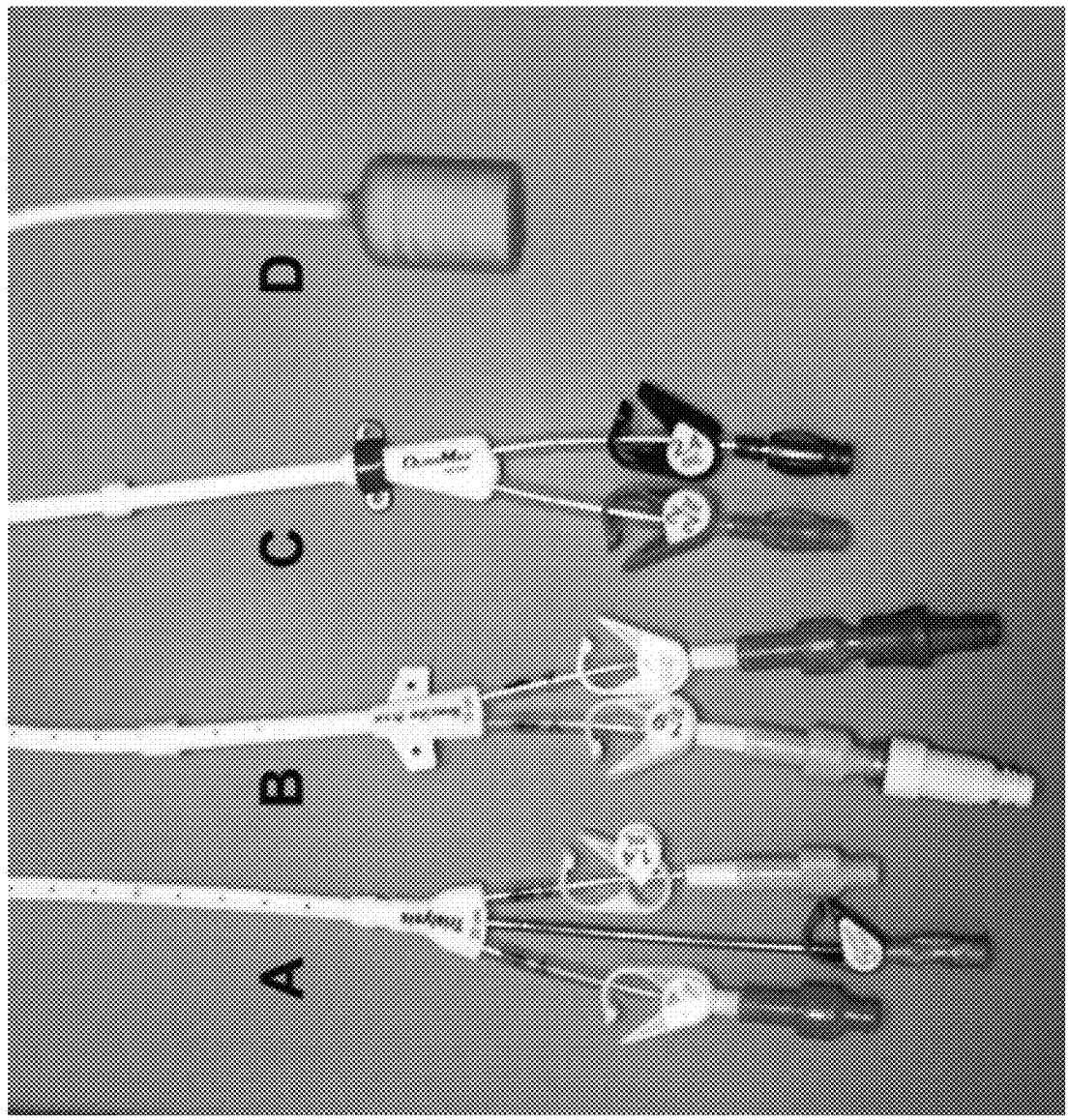
FIG. 14 illustrates examples of commercial dialysis catheters (A-C) and also a prototype of a double lumen catheter with a REStip type connector (D).

The present invention is further directed to a unique fitting for improving catheter access. This unique fitting, referred to herein as a REStip, consolidates all external components of an intravascular catheter, including: needleless connectors, luer hubs, extension tubing, and clamps; and is intended to replace only the distal portion of the catheter—leaving the indwelling catheter unchanged (thereby compatible with all existing intravascular catheters). Thus, during the manufacturing process, catheters employing this system will be outfitted with the REStip connector versus the common molded bifurcation and extension tubing. FIG. 14 illustrates examples of commercial dialysis catheters (A-C) and also a prototype of a double lumen catheter with a REStip type connector (D). Catheter B is shown with two different commercial needleless connectors.

Figure 15:
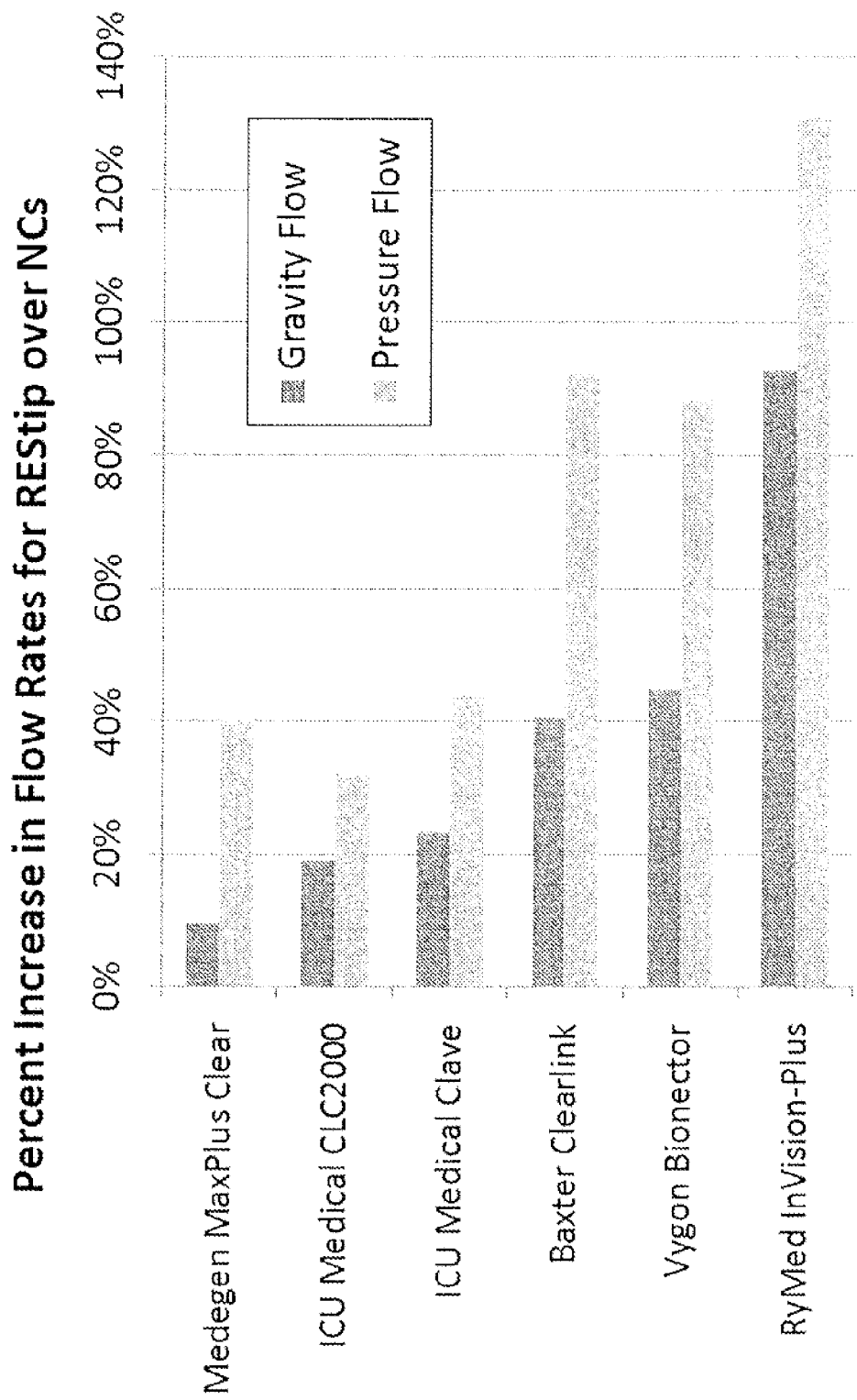
FIG. 15 illustrates a graphical view of a percent increase in flow rates for the REStip over needleless connectors.

The current REStip prototype reduces priming volume of common dialysis catheters by up to 55% as evidenced by Table 1, below. This reduction in priming volume is not only a reduction in surface area prone to bacterial attachment but beneficial for clinical applications where very low priming volumes and dead space are required. The double lumen REStip connector has a 14 gauge fitting which improves flow rate by as much as 93% for gravity-fed lines and 131% for pressure (300 mmHg) injections over current catheters using needleless connectors. FIG. 15 illustrates a graphical view of a percent increase in flow rates for the REStip over needleless connectors.

TABLE 1

Reduction in priming volume for commercial catheters using REStip

| Catheter | Segment | Size (F) | Length (cm) | Lumen(s) | Reduction in Priming Volume (%) |
|---|---|---|---|---|---|
| Bard Trialysis | Dialysis (ST) | 13 | 20 | 3 | 54.3% |
| Bard DuoGlide | Dialysis (ST) | 13 | 15 | 2 | 54.6% |
| Bard HemoStar XK | Dialysis (LT) | 16 | 19 | 2 | 32.5% |

TABLE 1-continued

Reduction in priming volume for commercial catheters using REStip

| Catheter | Segment | Size (F) | Length (cm) | Lumen(s) | Reduction in Priming Volume (%) |
|---|---|---|---|---|---|
| AngioDynamics DuraMax VP | Dialysis (LT) | 15.5 | 32 | 2 | 26.1% |
| Bard Hickman | CVC | 9.6 | 56 | 1 | 43.3% |
| Bard PowerHickman | CVC | 8 | 47 | 1 | 37.2% |

LEGEND:
Short-Term(ST),
Long-Term(LT)

Figure 16A:
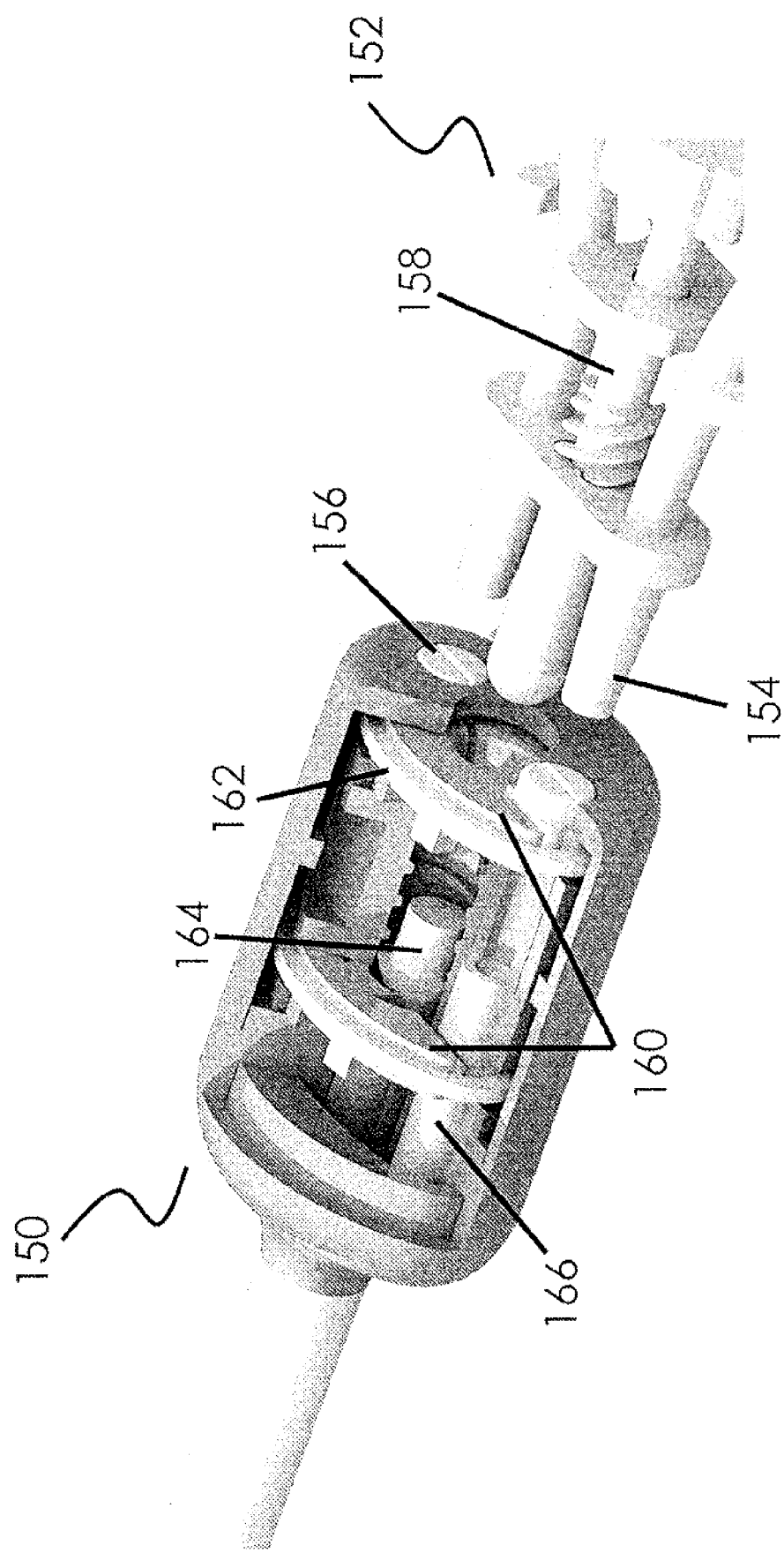
FIGS. 16A and 16B illustrate a double lumen design illustrating a mechanism by which the septa of the device are maintained.
Figure 16B:
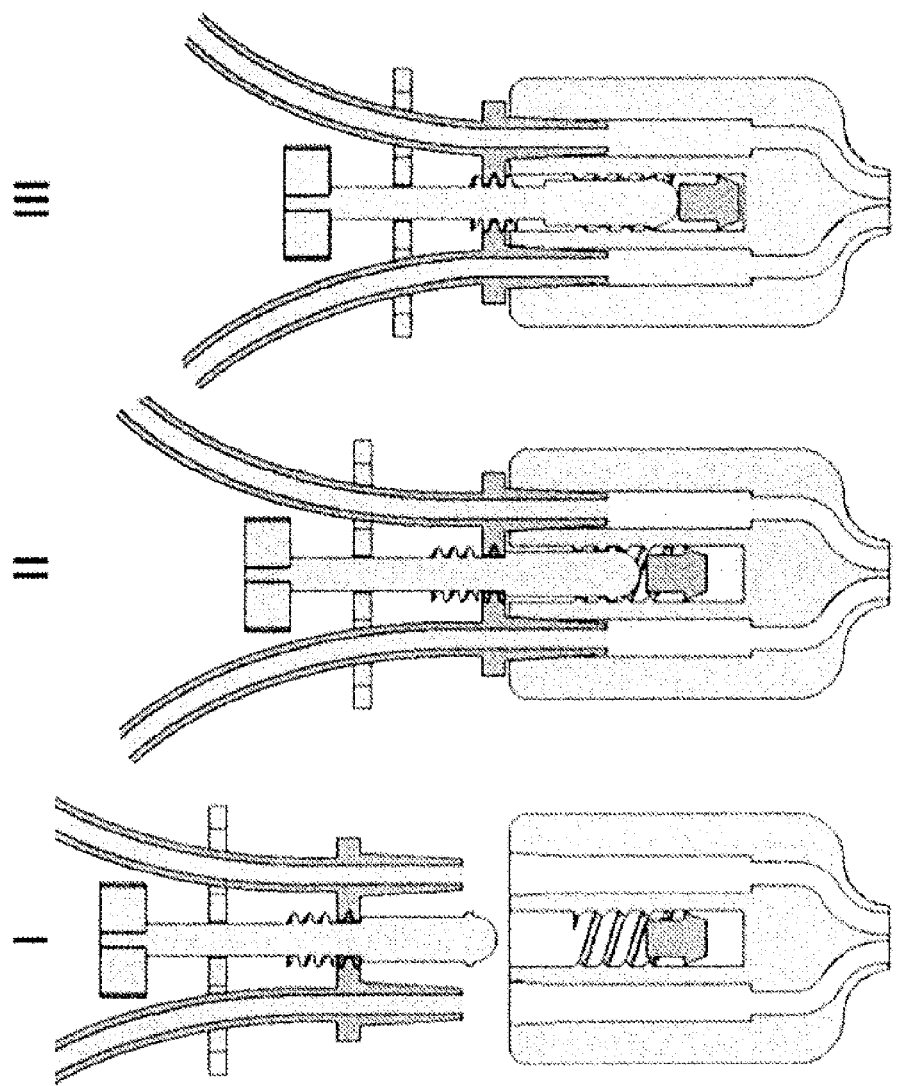

FIGS. 16A and 16B illustrate a double lumen design illustrating a mechanism by which the septa of the device are maintained. For the double lumen design illustrated in FIGS. 16A and 16B the septa are attached to a fixed slider that returns to a predetermined position following detachment of the connection assembly by an elastic band. All other needleless connectors currently on the market rely either on the spring force of a silicone septum or secondary septum layer or a physical spring to reset the septum.

More particularly, FIG. 16A illustrates a cutaway view of the REStip connector 150. The disposable extensions assembly 152 contains luer fittings 154 and an opening component, or plunger 158. Silicon septa 156 are opened when plunger 158 displaces the slider/clamps 160 which are held together by an elastic band 162. After luer fittings are seated the plunger continues and engages the depressor 164 which releases the clamp 160 on the compressible lumen 166 opening the fluid conduit.

FIG. 16B illustrates the phases of attaching the disposable extensions to the connector. In FIG. 16B, Phase I shows the extension assembly before engaging with the REStip connector. (The plunger extends further than the lumen line(s) to first open the septa/um prior to the luer taper.) Between Phase I and II, the assembly is advanced into the REStip connector by the luer threads. The one-piece stator from which the lumens extend has an opening such that the plunger can freely rotate as it engages with the internal luer threads. In Phase II, the luer taper is fully seated with the internal luer taper of the REStip connector and forms a water-tight seal, yet the lumens are still closed because of the clamps downstream. In Phase III, the plunger engages a depressor that opens the clamps on the internal tubing below. (The reason for internal tubing is to maintain a sterile system; an obstruction to the fluid path such as a valve could get contaminated given the present design.) A second set of threads on the plunger mesh with matching features on the stator to ensure the assembly remains fixed and the luer taper(s) do not unseat while the clamps are released. Detachment of the extension set occurs in the reverse process: the depressor is released and clamps are closed; the luer taper becomes unseated; and the septa on the sliders reseal.

The design of the elastic band/slider mechanism has lent itself to adding additional functionality, namely a clamping mechanism. Recall in FIG. 14, all catheters require both a cap (most often in the form of a needleless connector, FIG. 14B) and a clamp. The REStip connector integrates both, which provides all necessary protections against device leakage.

There is a second benefit to the two-tiered system of REStip over the standard-of-care needleless connectors: a neutral reflux device without concerns of a clamping sequence. The design of a particular needleless connector will determine if it is a positive, negative, or neutral displacement device. Because catheter tip reflux is undesirable (both positive and negative can lead to device malfunction, occlusion, and infection), all care providers must be aware of which devices they are using, which will dictate the sequence of clamping and detaching of administration lines. Positive and negative displacement devices must be clamped prior to removing lines or reflux will occur; neutral displacement devices do not require a particular sequence.

The device is not limited to the double lumen design of FIGS. 16A and 16B. Single and multi-lumen designs are possible. The current double lumen design shows two planar sliders/clamps held together by a single elastic means, but it is feasible to accomplish the same function with only one slider/clamp, and with more than two. The drawings are intended only to show the process of translating an axial motion into opening members in an orthogonal plane, which are reset by an elastic outer force.

Figure 17:
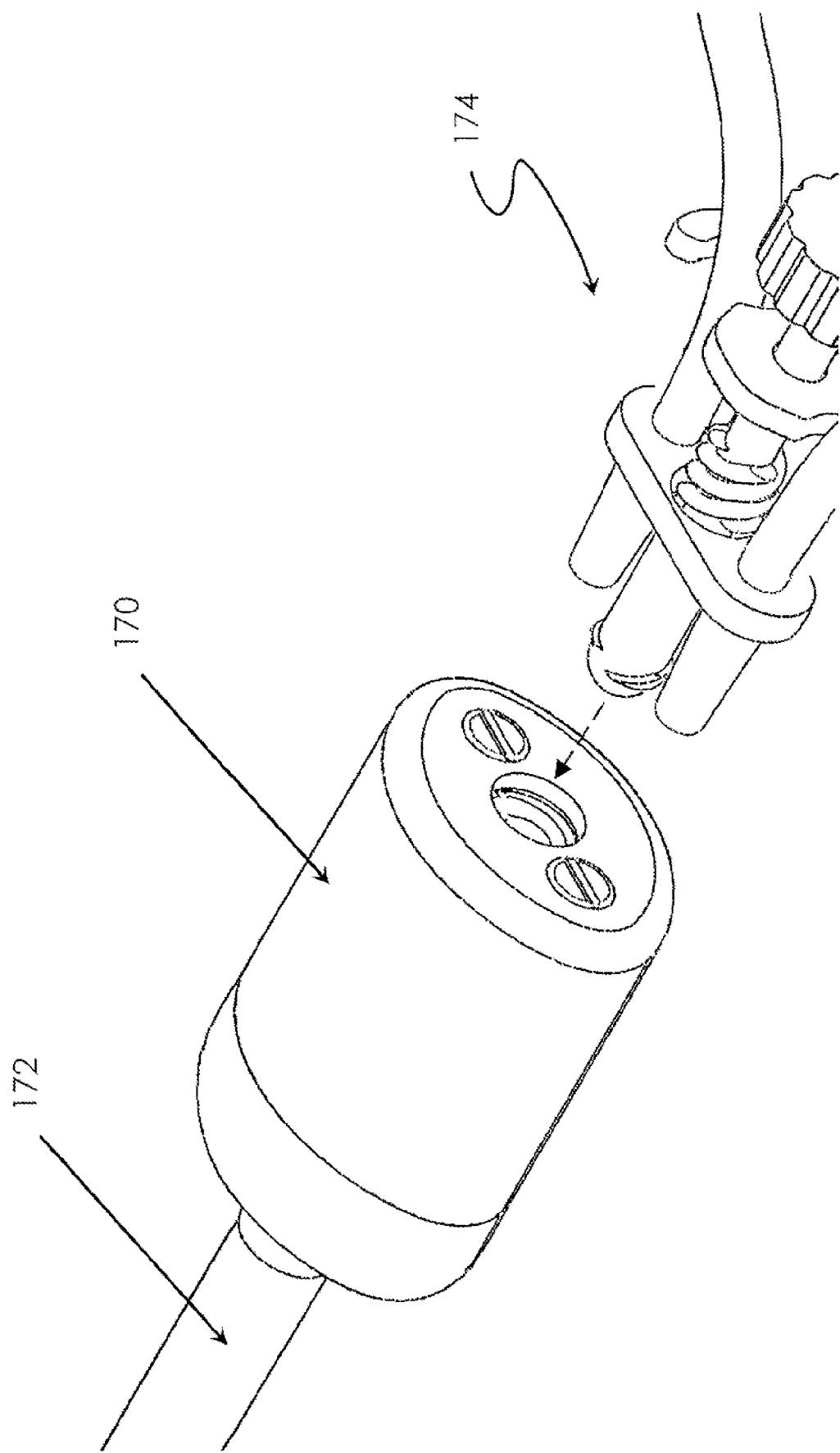
FIG. 17 illustrates a perspective view of a connector according to an embodiment of the present invention.

FIG. 17 illustrates a perspective view of a connector according to an embodiment of the present invention. As illustrated in FIG. 17 the REStip connector 170 is a distal adapter for a percutaneous catheter 172. The REStip connector relies on a unique extension fitting 174.

Figure 18:
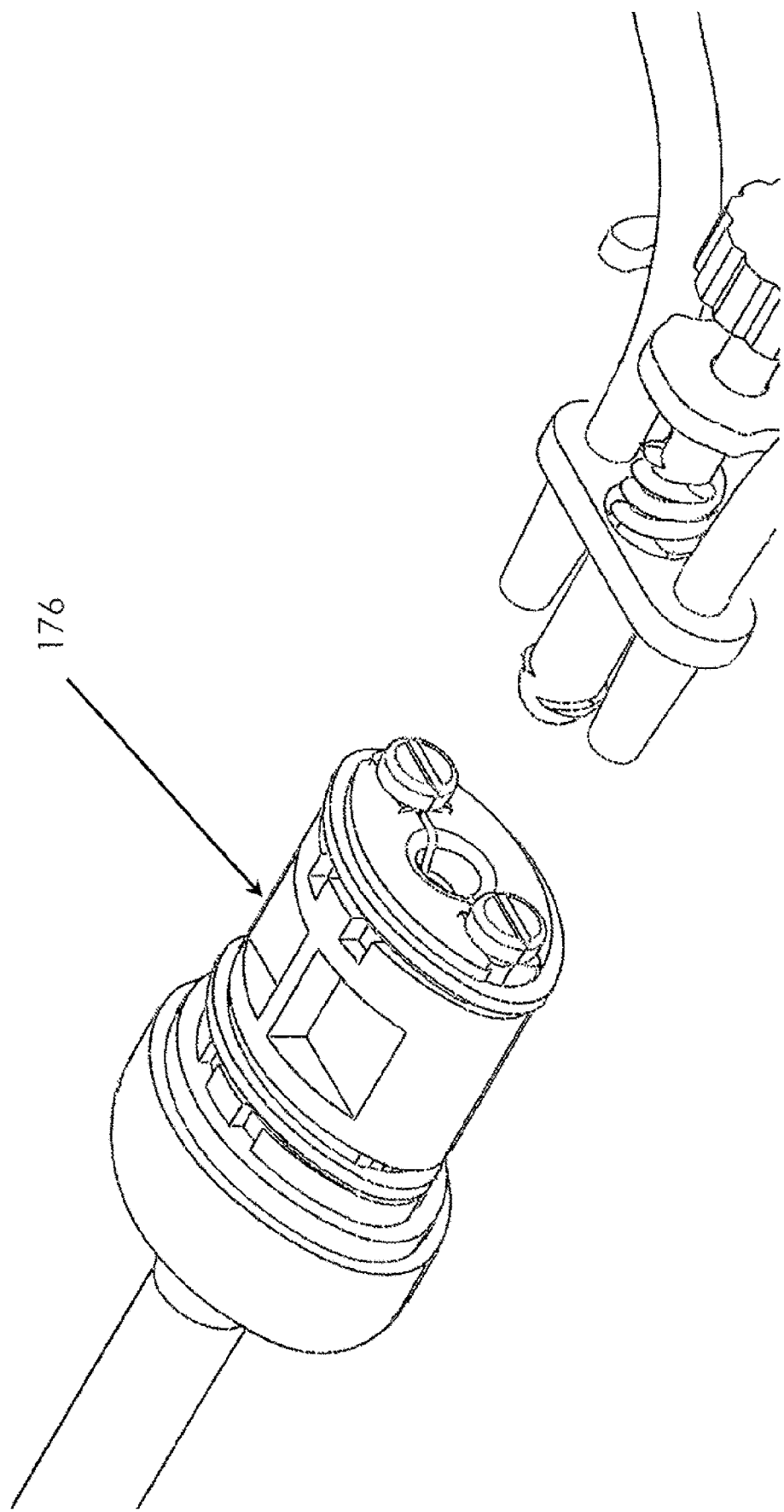
FIG. 18 illustrates a perspective view of a connector according to an embodiment of the present invention, wherein an outer covering of the connector has been removed.

FIG. 18 illustrates a perspective view of a connector according to an embodiment of the present invention, wherein an outer covering of the connector has been removed. As illustrated in FIG. 18, the REStip connector 170 includes a molded base assembly 176. Features of the base assembly will be described in more detail with respect to additional figures herein.

Figure 19:
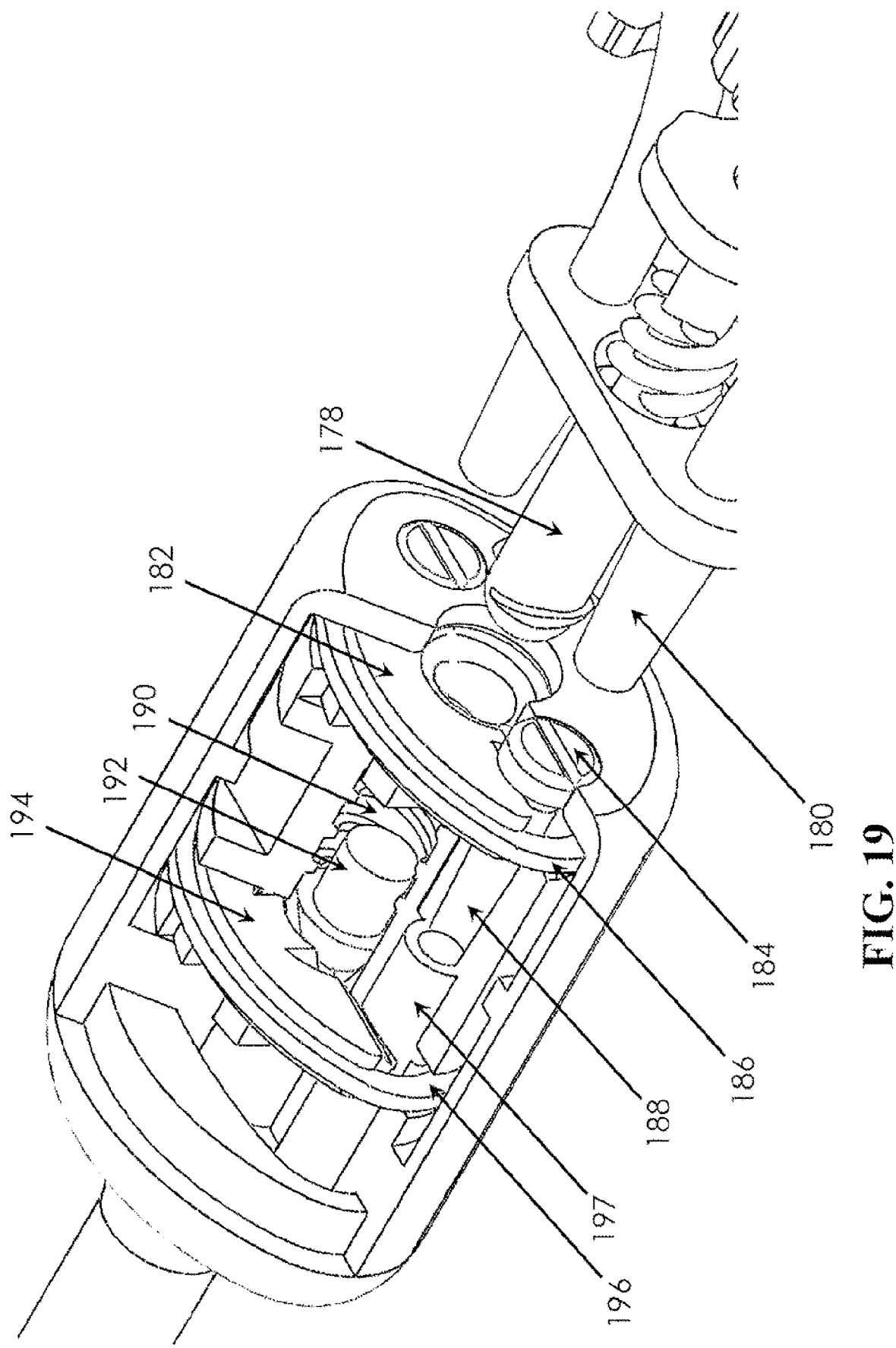
FIG. 19 illustrates a partially sectional view of a connector according to an embodiment of the present invention.

FIG. 19 illustrates a partially sectional view of a connector according to an embodiment of the present invention. A plunger 178 of the disposable extension assembly extends further than luer tapers 180. As the extension fitting is brought near the distal connector the plunger engages with a slider mechanism 182. The current configuration has two sliders, each with two half-septa 184. Single, double, and triple lumen connectors may require more or less sliders. The slider(s) are planar and held together by an elastic band 186, which stretches as the sliders are displaced from the engaging plunger. The displacement of the slider/septa component opens lumen access for the luer taper. In the closed configuration (shown) the septa seal the distal lumens 188.

Further with respect to FIG. 19, the internal channel of the REStip connector has luer threads 190 for securing the plunger 178 and extension fitting. In one configuration (shown) a depressor 192 is contained within, though this part provides only a lengthening of the plunger for opening the lower clamps 194. The planar clamps 194 are held together by an elastic band 196 and clamp flexible internal tubing 197. In the same fashion as the slider mechanism, the clamps are displaced by an opening member (the depressor in the current drawing).

Figure 20:
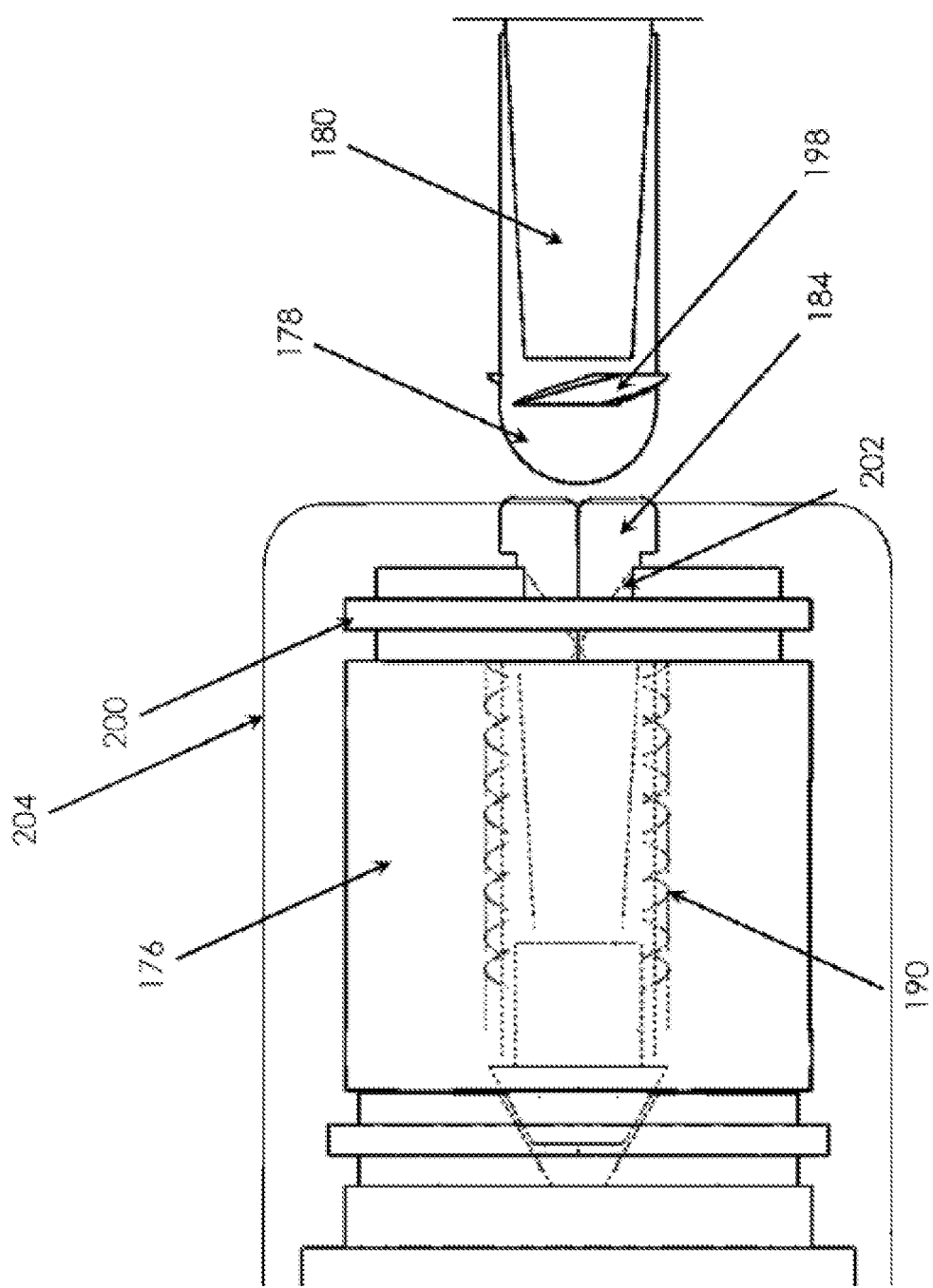
FIG. 20 illustrates a side view of a distal connector and extension fitting, according to an embodiment of the present invention.

FIG. 20 illustrates a side view of a distal connector and extension fitting, according to an embodiment of the present invention. Further, FIG. 20 illustrates stage 1 of 4 stages, pre-connection of an extension fitting, with the connector in a sealed configuration. The plunger 178 is shown to extend further than the luer taper 180. The plunger is shown to have luer threads 198. In the closed state the septa 184 are sealed. The slider mechanism 200, consisting of both the slider and elastic band, is in the closed state. The slider mechanism 200 has a sloped region 202 to transfer the horizontal motion of the plunger into an orthogonal motion of the slider mechanism. This action opens the septa/um. The outer shell 204 is faintly drawn for reference. (FIGS. 21-23 do not show the internal threads 190 of the molded base assembly 176 for clarity.)

Figure 21:
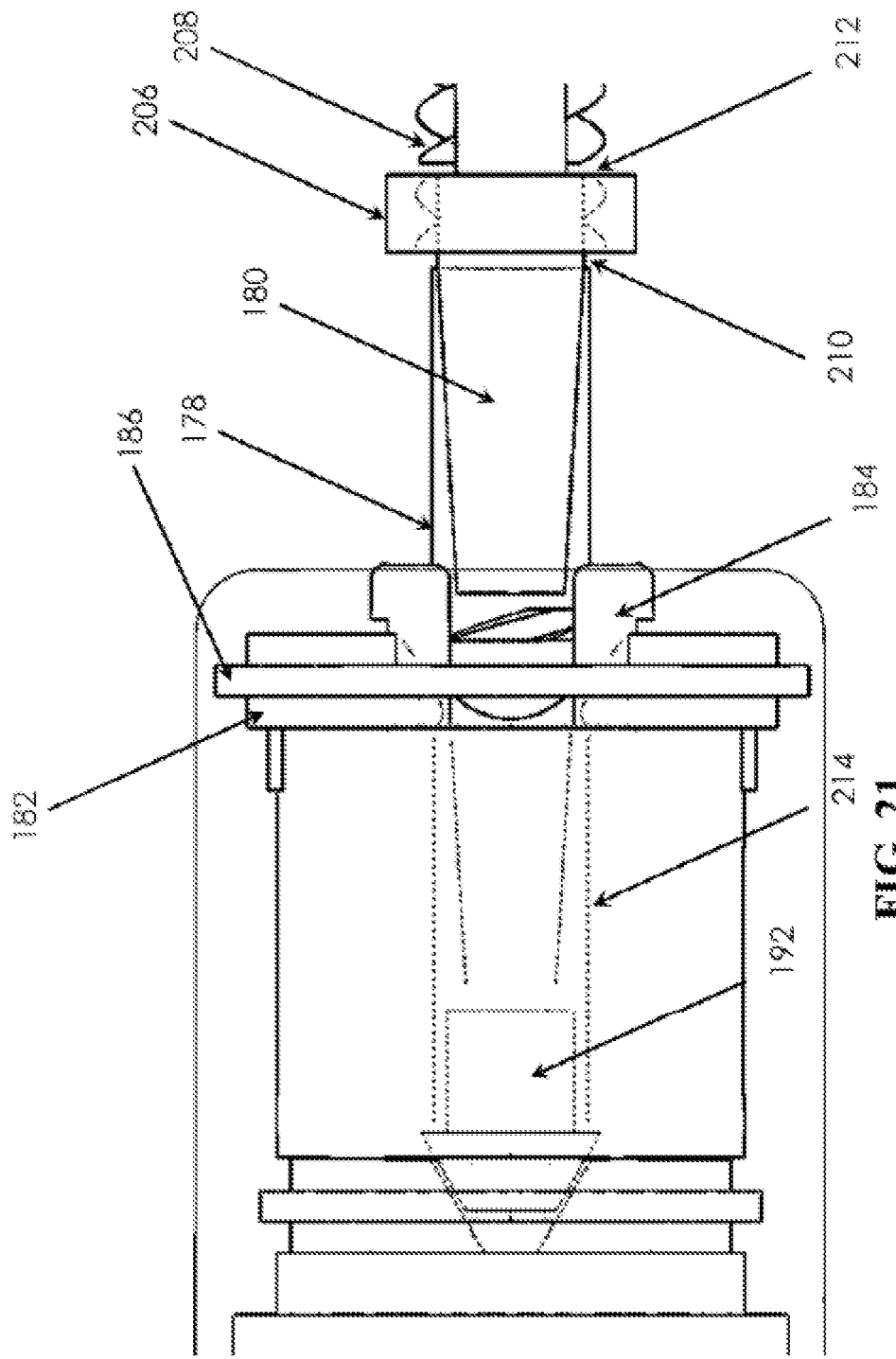
FIG. 21 illustrates a side view of a distal connector and extension fitting, according to an embodiment of the present invention.

FIG. 21 illustrates a side view of a distal connector and extension fitting, according to an embodiment of the present invention. Further, FIG. 21 illustrates stage 2 of 4 stages, opening of the septa/um. The plunger 178 extends at least the length to open the septum prior to the attachment of the luer taper 180 in order that the luer taper tip does not come in contact with the outer surface of the septum. The luer taper 180 is attached to a stator 206 that allows the plunger 178 of the extension assembly to freely rotate. The stator is maintained between the plunger 178 and second thread set 208, illustrated with gaps 210 and 212. The inner cavity 214 through which the plunger advances has been shown sans luer threads for clarity.

Figure 22:
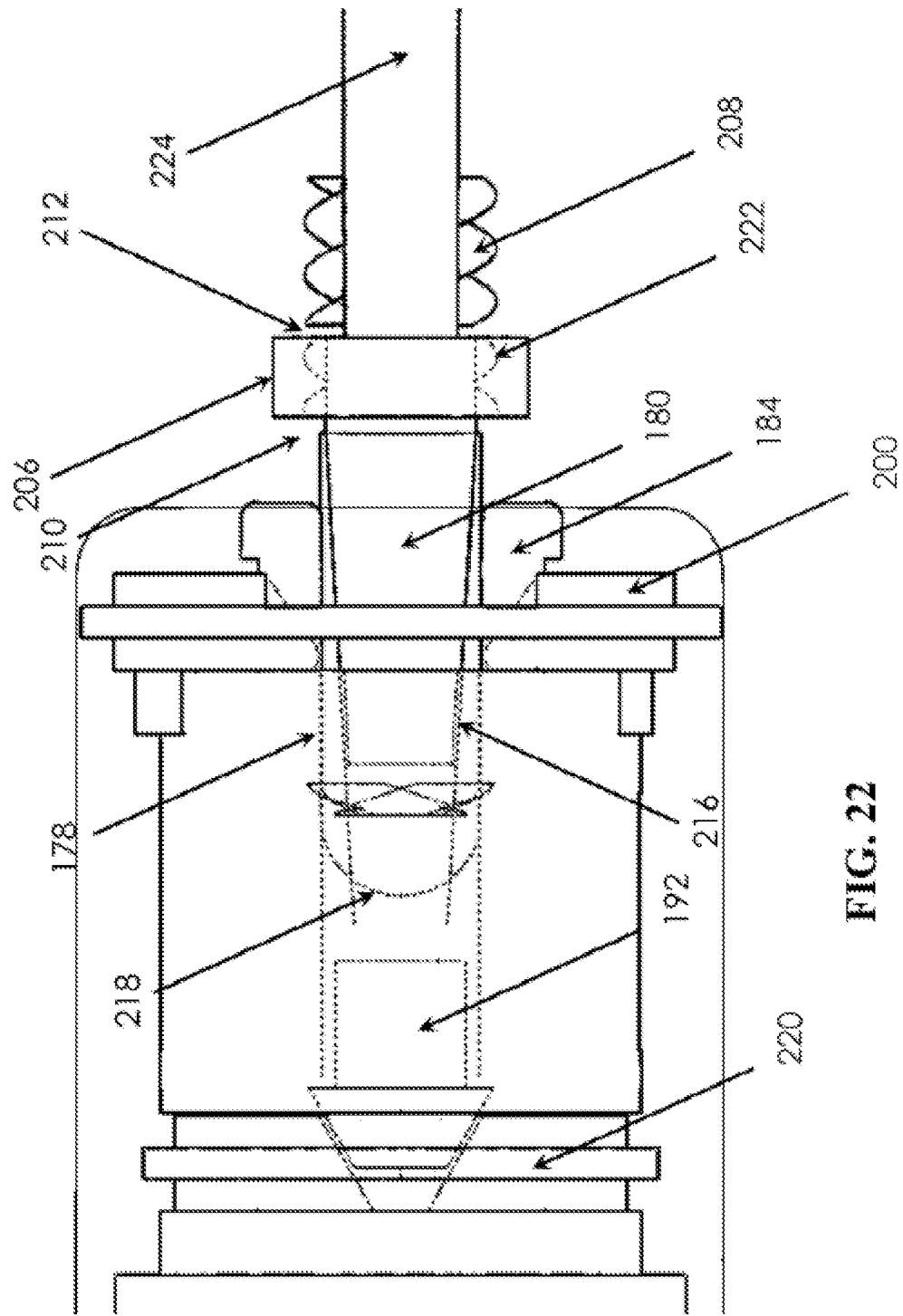
FIG. 22 illustrates a side view of a distal connector and extension fitting, according to an embodiment of the present invention.

FIG. 22 illustrates a side view of a distal connector and extension fitting, according to an embodiment of the present invention. Further, FIG. 22 illustrates stage 3 of 4 stages, seating of the luer taper. The drawing shows the seating of the luer taper 180 with internal luer channel 216 of the molded base unit. Seating of the luer taper occurs prior to the plunger tip 218 engaging with the depressor 192. This is to ensure that a water-tight seal is maintained prior to the releasing of the clamping mechanism 220. In some configurations the plunger tip 218 may act as the depressor for opening the internal clamping mechanism 220, which consists of a clamp and elastic band. The slider mechanism 200 is fully opened. The luer threads on the plunger 178 are engaged with matching internal luer threads (not shown for clarity). The stator 206 is still disposed between the plunger and second thread set 208 as shown by the gaps 210 and 212. The stator has internal features 222 for receiving the second thread set 208. In one embodiment, the internal features 222 are matching threads with a resisting component such as a silicon liner (reducing the thread size) or plastic stopper, which prevent the thread set 208 from advancing into the stator 206 prior to seating of the luer taper. Flexible extension tubes 224 extend from the stator for connecting with medical equipment.

Figure 23:
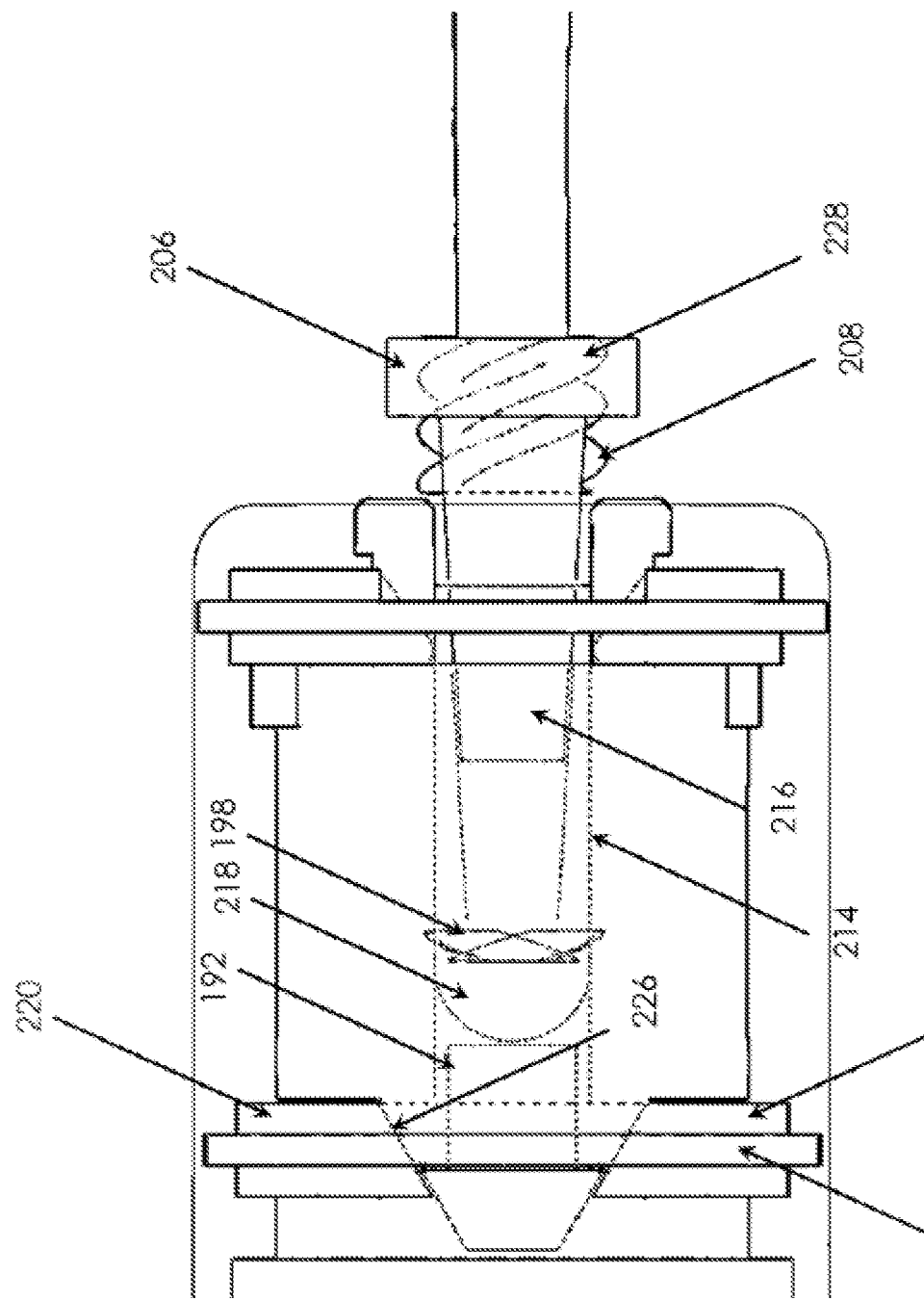
FIG. 23 illustrates a side view of a distal connector and extension fitting, according to an embodiment of the present invention.

FIG. 23 illustrates a side view of a distal connector and extension fitting, according to an embodiment of the present invention. Further, FIG. 23 illustrates stage 4 of 4 stages, releasing of the internal clamps. The internal clamp mechanism 220 opens orthogonally with the depressor 192 along a sloped line 226. In one embodiment, the plunger tip 218 has engaged the depressor 192; in another embodiment, the plunger tip acts as the depressor. The advancement of the plunger through the internal cavity 214 does not cause torsional tension on the seated luer threads 216 due to the tolerance of the internal features of the stator 206. The threads on the plunger 198 are engaged with internal threads of the molded base unit (not shown for clarity) which prevents lateral movement of the extension assembly. The second thread set 208 that is engaged 228 with the stator 206 locks the extension assembly together so that the luer taper does not become unseated.

In this final stage of the connection process, the luer tapers are seated with internal luer tapers and clamps are released, permitting patent access to the indwelling catheter. The detachment process is a complete reversal of the attachment stages: the depressor is released, causing the clamps to close the internal flexible tubing; the plunger retracts and unseats the luer tapers; the septa/um reseal.

For the present invention, a catheter with removable extensions having been initially attached and resembling a common percutaneous catheter, is inserted into a patient by one skilled in the art. Following normal clinical technique, the catheter is checked for patency, flushed, primed with a fluid solution, and secured to the patent's skin through a preferred securement means. If the catheter is not required for immediate clinical use, the extensions may be removed; remaining is a low-profile sealed catheter hub secured adjacent to the insertion site. Protection from environmental pathogens may be more easily safeguarded as the entire extravascular portion of the catheter, including the low-profile catheter hub and proximal insertion site, can be completely covered by a small sterile bandage, whereas this is unfeasible for current percutaneous catheters having non-removable extensions.

The extension connector and catheter hub are universally compatible for all multi-lumen catheters having an equal number of fluid connection fittings, irrespective of the number of lumens required for a particular clinical application. In a preferred embodiment, a multi-lumen catheter having three lumens, for example, has a universal triple-lumen extension connector. For clinical applications requiring less lumens than the total number of lumens of the multi-lumen catheter (i.e., one or two for said example), a particular disposable extension set with the desired number of lumen extensions is selected and non-functional lumens are plugged in the extension connection. More specifically, if single lumen access is needed for a triple lumen catheter, the healthcare professional has available a disposable extension set with only one single lumen extension, where the remaining two frustoconical members are non-patent. In this way, disposable triple lumen extension sets may not always be required, and thus reduce the cost and associated waste by the end user. To state this further, all double lumen catheters use a universal double lumen extension connector that may contain one or two extensions; all triple lumen catheters use a universal triple lumen extension connector that may contain one, two, or three extensions, and so forth.

Other disposable medical devices may be configured with the key-type connector, such as the molded tip of a syringe. The key-type connector may alternatively exist as a disposable standalone adapter for connecting other medical equipment without use of the extensions.

Pre-packaged, single-use extension sets may be pre-primed with a standard medical fluid, such as saline, so as to eliminate the need to prime the extensions prior to attaching the extension connector to the catheter hub, and thereby minimize risk of contamination or air embolism. The catheter hub may further have a transparent region or contain an indicator to inform the healthcare professional of the presence of air within the hub or in the immediate extravascular portion. Each single lumen extension comprises a luer fitting, for the attachment of medical equipment, a cap, and a clamp; such components are common to all extensions on existing percutaneous catheters. The extension connector further includes a pull-away tab that both protects the fluid fittings from contamination and helps contain the primed solution when in packaging. The pull-away tab is removed prior to attaching the extension set to the catheter hub.

This connection system of removable extensions and self-sealing catheter hub can be used without undoing the catheter hub from its securement means. This system is intended to be adaptable to all forms of elongated percutaneous medical articles including all indwelling, intragastric, intravascular, and urethral type catheters.

It is also conceivable to make the REStip connector a three tier system where the third layer is an additional clamp. Such design would be advantageous for adding a separable means to the REStip connector in the event an internal component failed (such as a broken elastic band). In this embodiment, the distal portion could be removed and the secondary clamp (most proximal to the indwelling catheter) would keep the internal lumens sealed until a replacement part is attached.

There is also an opportunity to create a needleless connector configuration of the disclosed technology. In this application the distal portion of the REStip connector is not molded to a catheter but a male luer fitting. This could give compatibility to current catheters and other medical articles where providers would desire the aseptic connection aspect of the design. Regulatory bodies may also be interested in creating a new standard that separates the luer device into two members.

Figure 24:
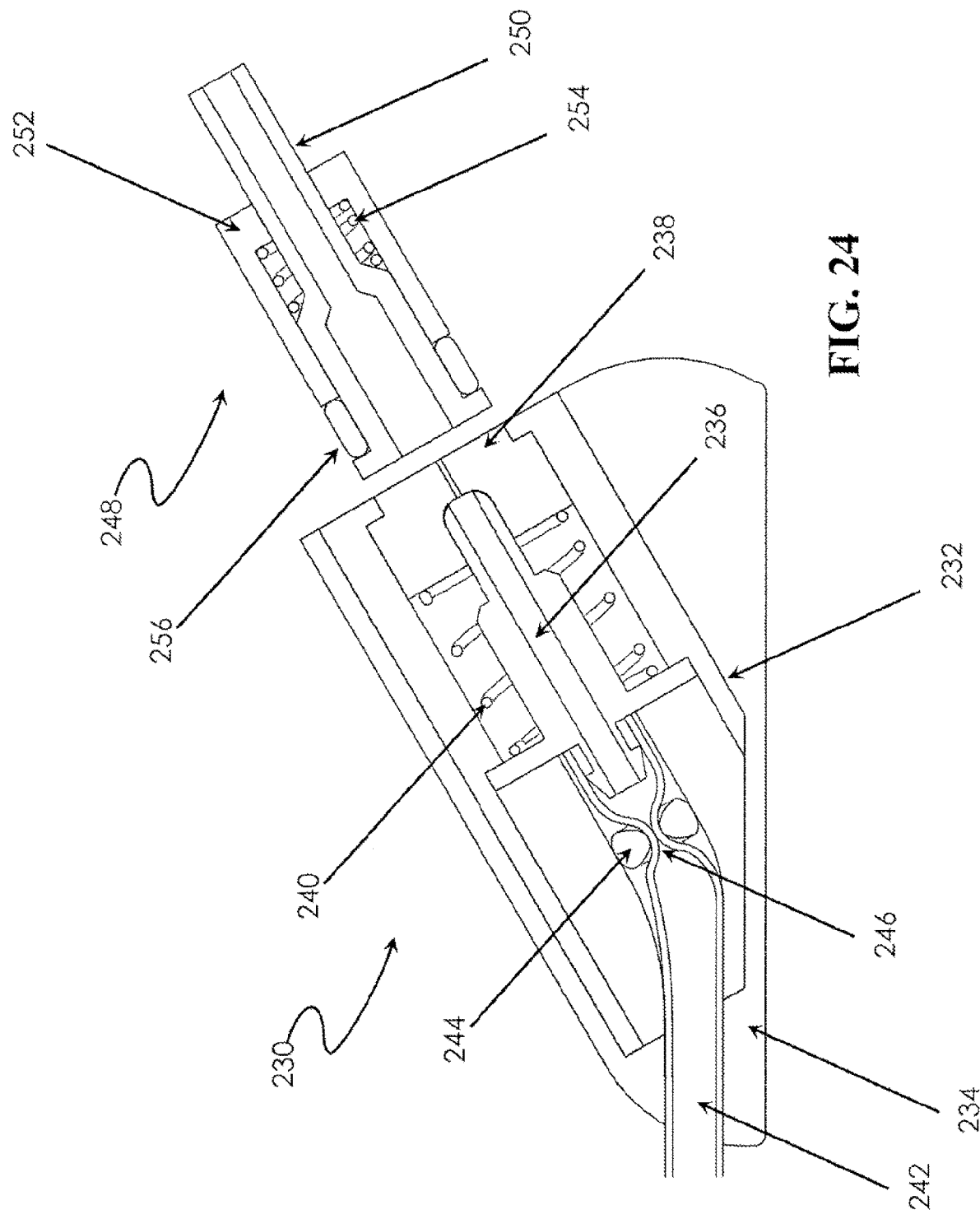
FIG. 24 illustrates a side view of a distal connector and extension fitting, according to an embodiment of the present invention.

FIG. 24 illustrates a side view of a distal connector and extension fitting, according to an embodiment of the present invention. The distal connector 230 includes a semi-rigid assembly 232 that houses multiple components and a soft over-molded portion 234. The figure shows a single lumen cannula 236 closed from outside contamination by a split-seal septum 238. The septum is maintained in the closed state by a spring or elastic mechanism 240. The internal cannula 236 joins with the indwelling portion of the catheter 242 and is molded into one piece by the soft outer housing 234. As is common to the art, the catheter 242 may be over-molded to a short section of tubing extending from the semi-rigid assembly 232. An elastic clamp 244 compresses the internal tubing 246 to prevent fluid movement and risk of air emboli. The elastic clamp opens with an intraluminal pressure exceeding normal physiologic venous pressure.

Further with respect to FIG. 24, an extension fitting 248 consists of a two-part unit with an inner component 250, which is continuous with the extension tubing (not shown), and an outer portion 252 that is displaced by both an internal elastic or spring-like mechanism 254 and an elastic gasket 256 that resides on the external portion of the inner component 250.

Figure 25:
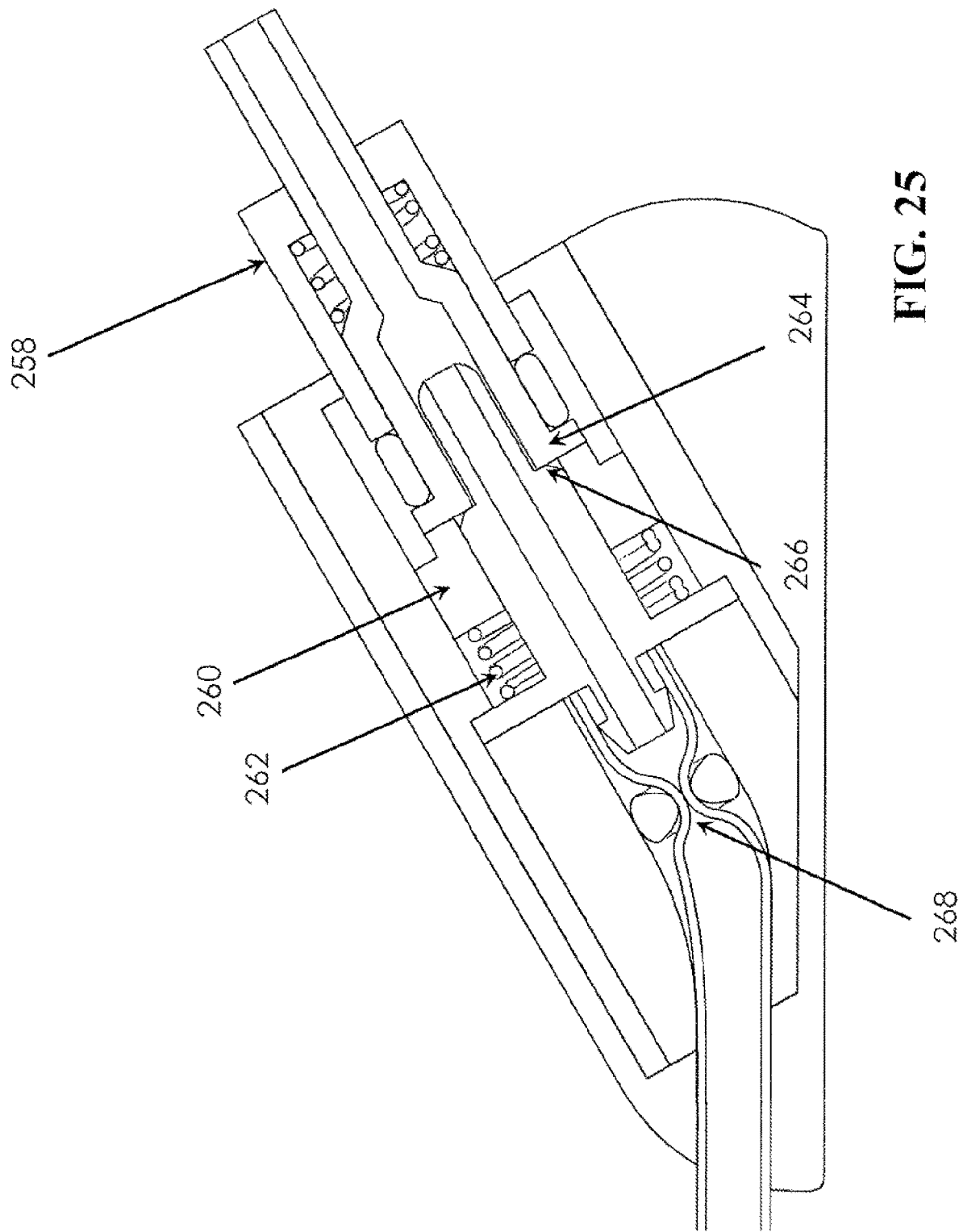
FIG. 25 illustrates a side view of a distal connector and extension fitting, according to an embodiment of the present invention.

FIG. 25 illustrates a side view of a distal connector and extension fitting, according to an embodiment of the present invention. The attachment of the extension fitting 258 displaces the split-seal septum 260 and compresses an inner spring 262. The inner component 264 of the extension fitting 258 seats on a portion of the inner cannula 266. The catheter to the patient remains clamped 268.

Figure 26:
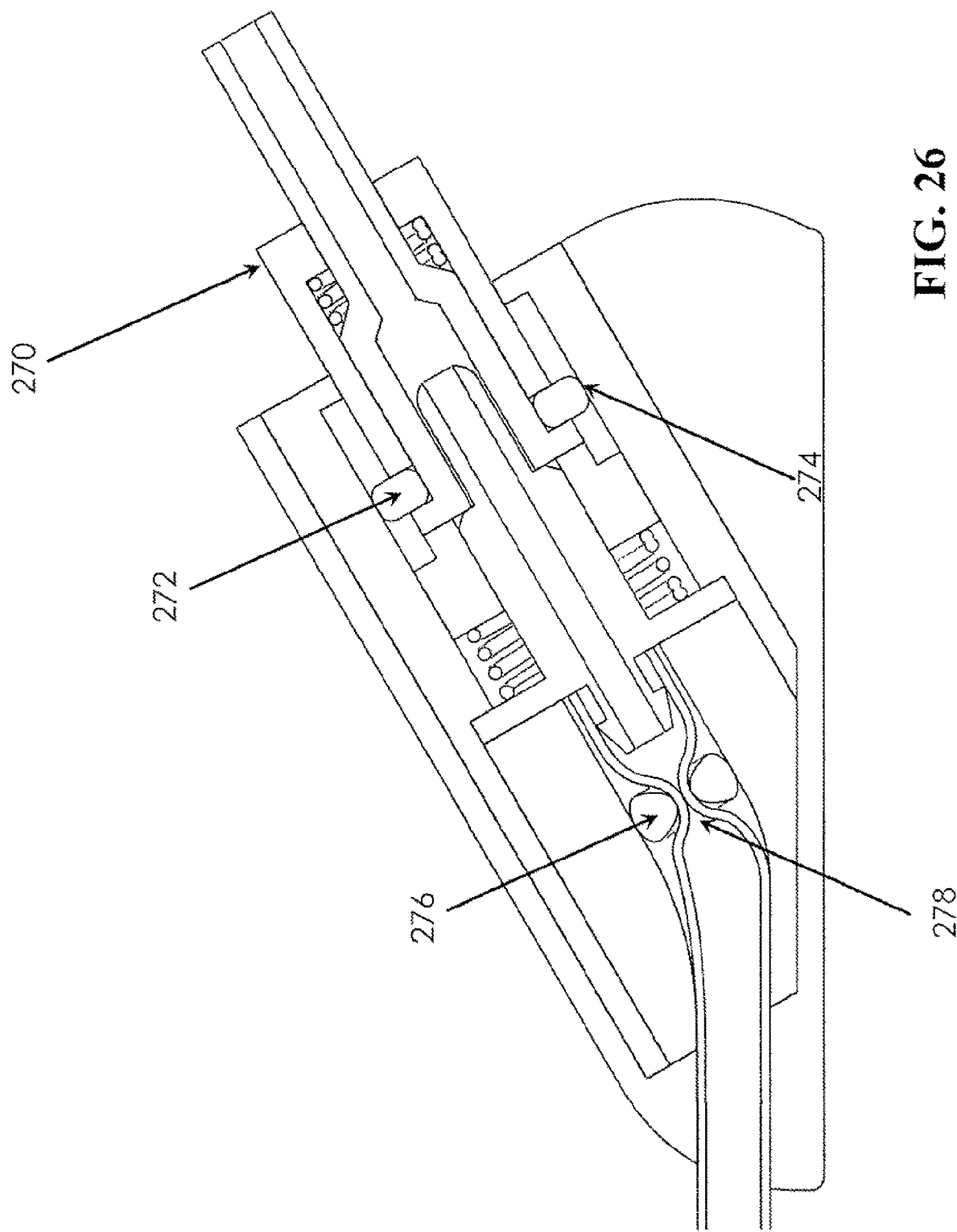
FIG. 26 illustrates a side view of a distal connector and extension fitting, according to an embodiment of the present invention.

FIG. 26 illustrates a side view of a distal connector and extension fitting, according to an embodiment of the present invention. After the extension fitting is seated against the internal cannula (recall FIG. 25), the outer component of the extension fitting 270 advances further to compress the gasket 272, creating a friction fit with the inner surface 274 of the semi-rigid housing. While intraluminal pressure from the catheter remains below the compression limit of the internal clamp 276 the catheter to the patient remains clamped 278.

Figure 27:
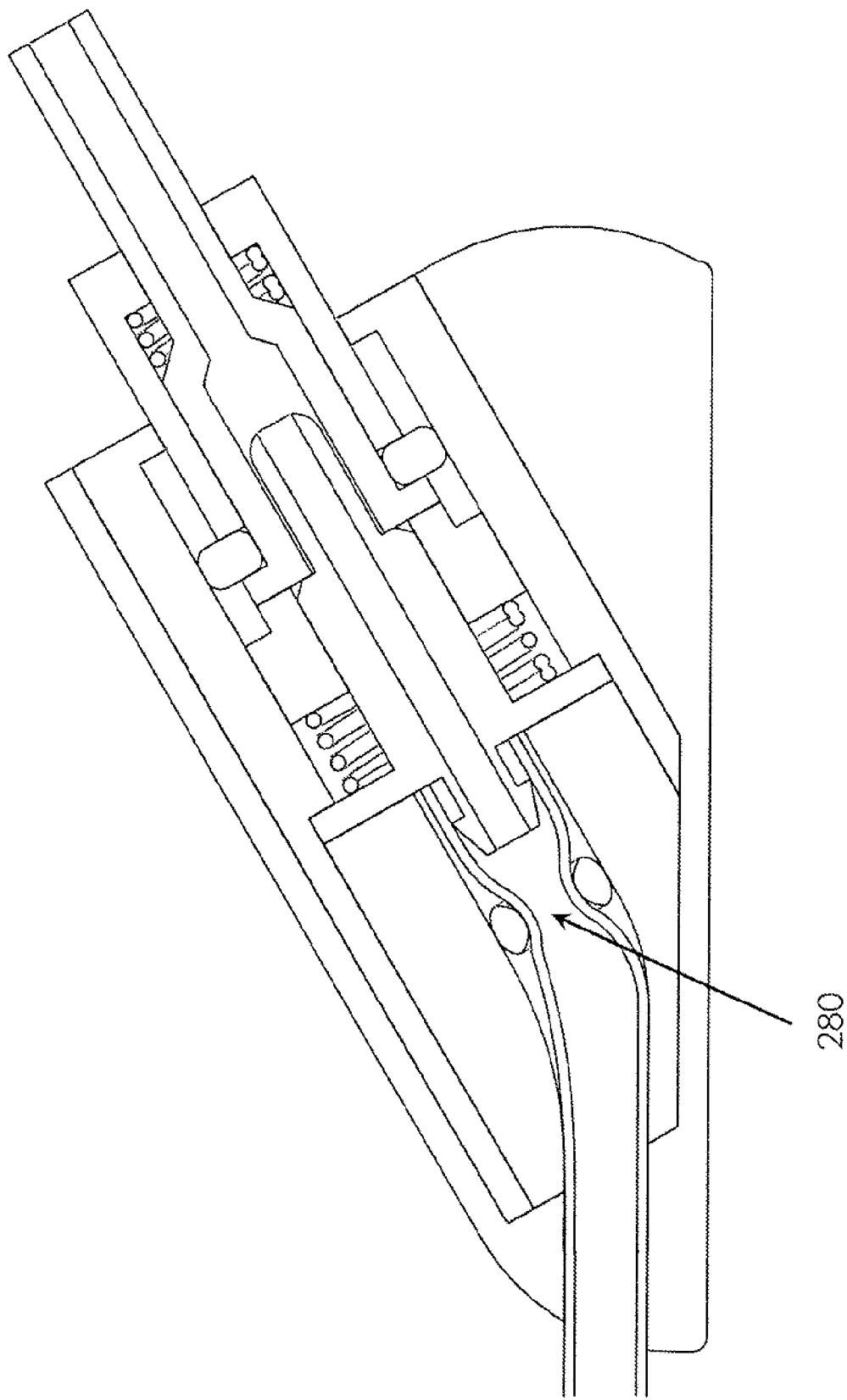
FIG. 27 illustrates a side view of a distal connector and extension fitting, according to an embodiment of the present invention.

FIG. 27 illustrates a side view of a distal connector and extension fitting, according to an embodiment of the present invention. During administration of fluids or drawing of blood samples, pressures exceeding normal physiologic central venous pressure (e.g., 10-20 mmHg) will exceed the compression limit of the internal clamp and open the catheter tubing 280.

The advantage of the elastic clamping mechanism on internal tubing as opposed to a valve system that resides in-line with the fluid lumen is that a valve can create areas of stagnancy and further provide geometric regions prone to encouraging bacterial adhesion and biofilm development. With respect to FIGS. 24-27, the clamp does not reside within the blood flow-field, but compresses the outer surface of the tubing.

Figure 28:
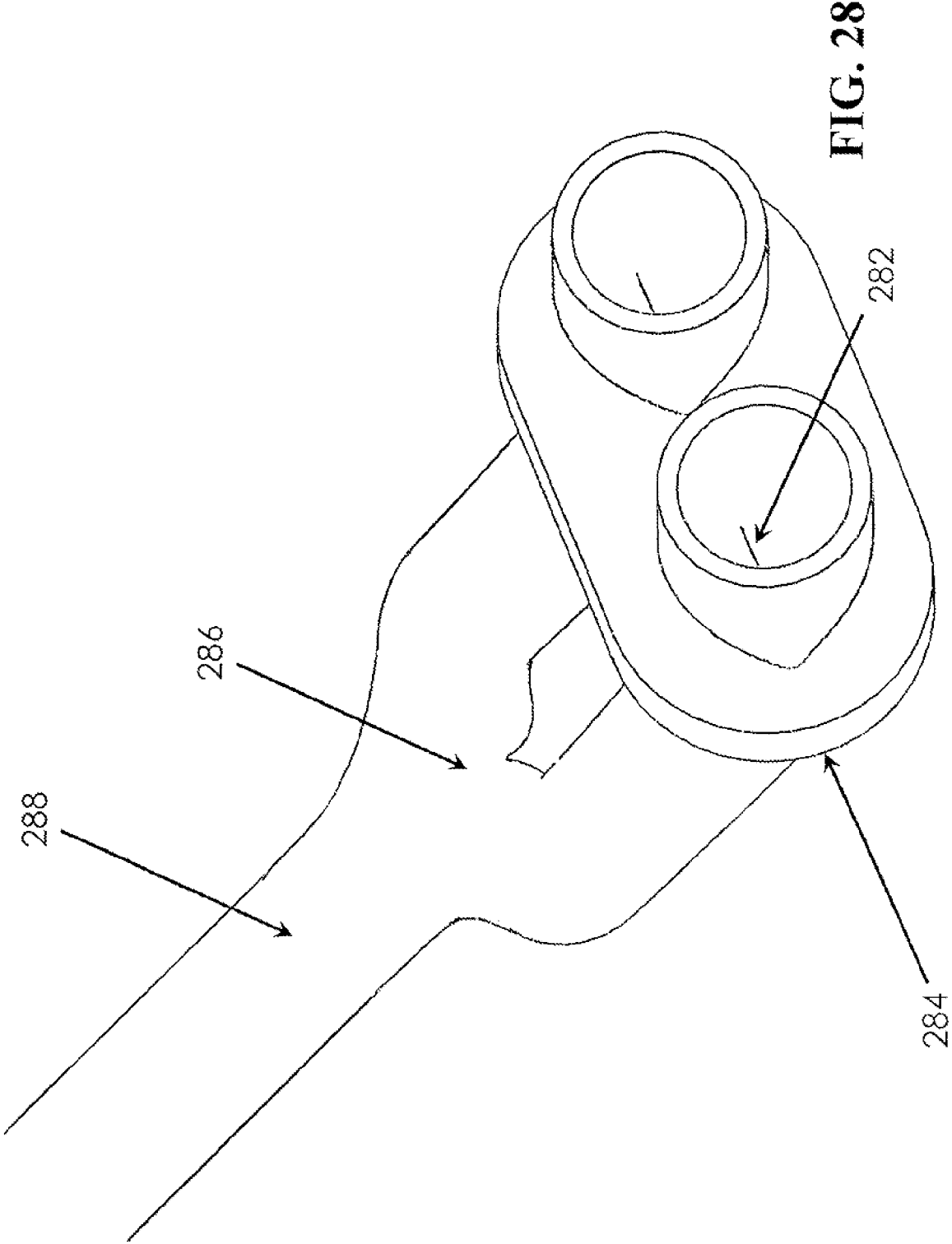
FIG. 28 illustrates a tube clamping mechanism for a double lumen catheter according to an embodiment of the present invention.

FIG. 28 illustrates a tube clamping mechanism for a double lumen catheter according to an embodiment of the present invention. The figure shows the section of tubing residing between the internal cannula and indwelling portion of the catheter (recall FIG. 24). The figure shows the clamping of a double lumen catheter by one or more slits 282 by a single elastic mechanism E3 prior to the bifurcation 286 of a multi-lumen catheter 288. It is conceivable that separate elastic clamping mechanisms could be individually applied to each single lumen line.

Figure 29:
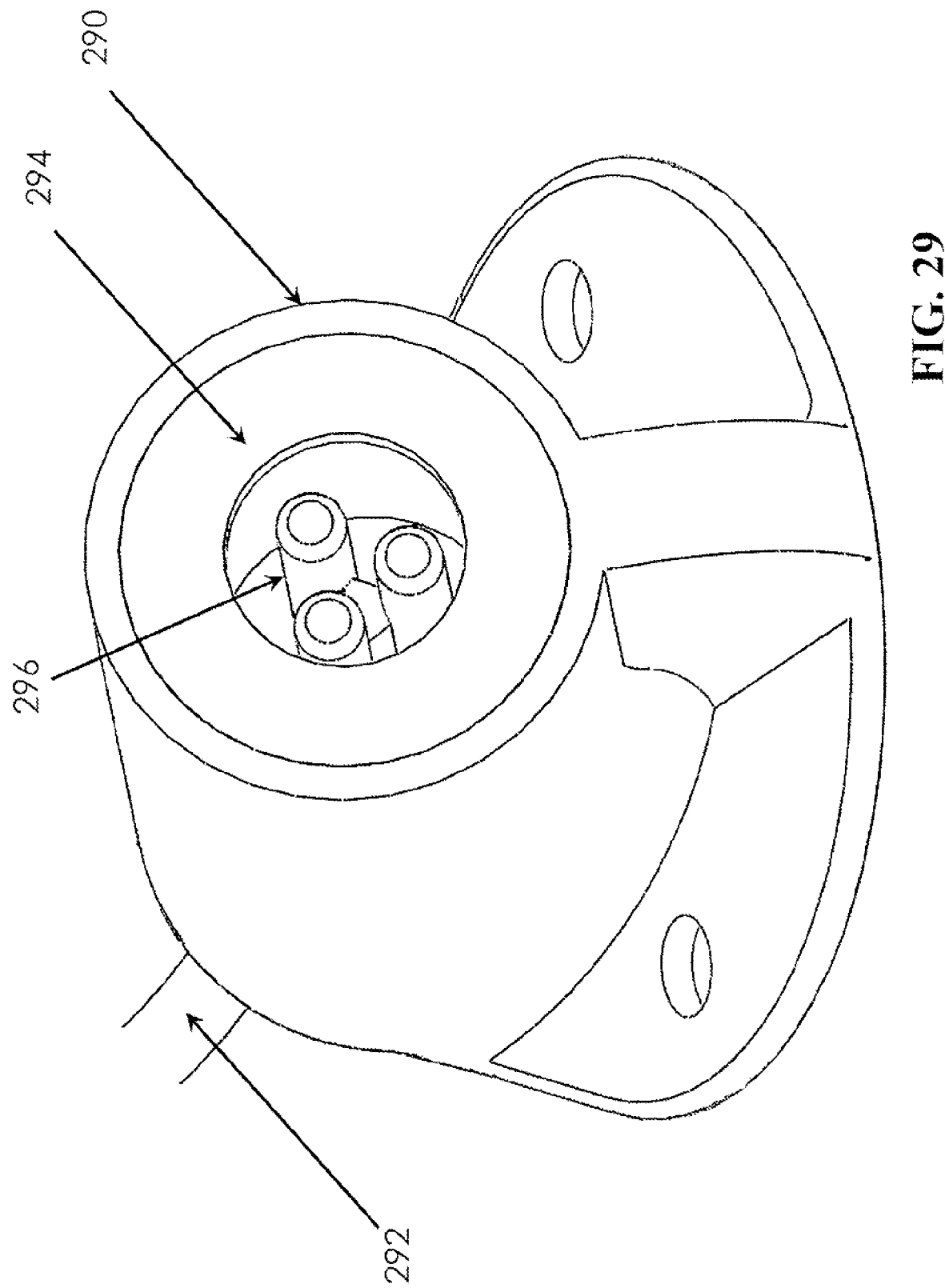
FIG. 29 illustrates a perspective view of a distal connector according to an embodiment of the present invention.

FIG. 29 illustrates a perspective view of a distal connector according to an embodiment of the present invention. The figure shows the distal catheter connector 290 of a triple lumen catheter 292, having a single opening 294 with three internal cannulas 296.

Further with respect to FIG. 29, and recalling FIGS. 25 & 26, the advancement of the inner component of the extension fitting as a linear translation (as opposed to a threaded luer locking mechanism which requires a torsional action of the inner component) enables the inner cannula component to be of 2 or more separate cannulas which remain aligned with the extension tubing of a multi-lumen catheter.

Figure 30:
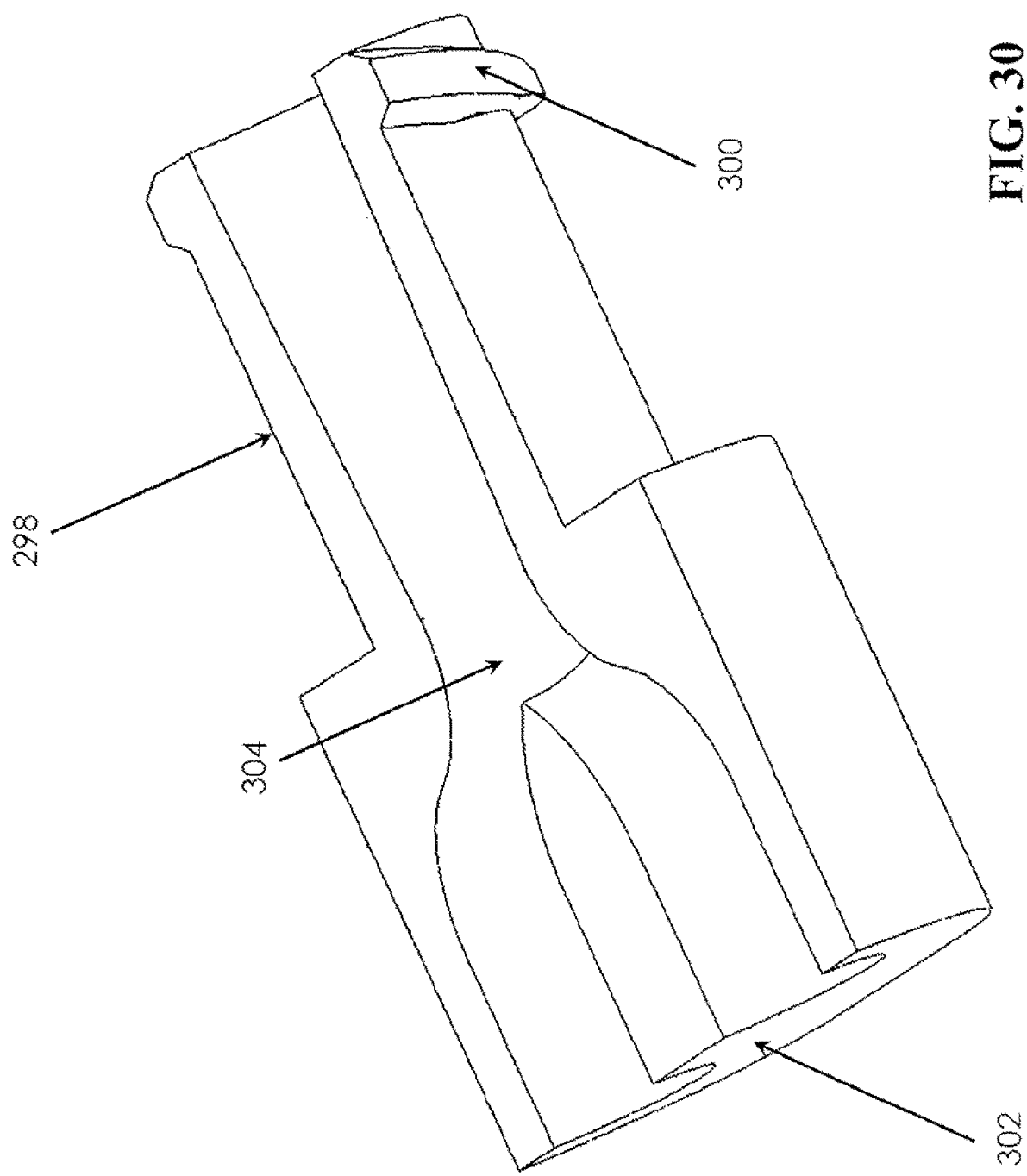
FIG. 30 illustrates a partially sectional view of a syringe adapter for flushing all lumens of a double lumen catheter, according to an embodiment of the present invention.

FIG. 30 illustrates a partially sectional view of a syringe adapter for flushing all lumens of a double lumen catheter, according to an embodiment of the present invention. The figure shows an adapter 298 for a standard luer syringe having a luer fitting 300 for connecting with a double lumen distal catheter connector 302. The adapter bifurcation 304 from the single channel into a multi-lumen channel to allow a provider to flush all lumens of the catheter with a single action from a standard syringe.

Further with respect to FIG. 30, the adapter may be configured with a valve system or be used with a single syringe having three separate channels, e.g., to ensure a higher flow resistance in one lumen of the multi-lumen catheter (such as from a catheter occlusion) does not redirect flow to the other lumens, but instead ensures all lumens are flushed with an equal volume of fluid.

Figure 31:
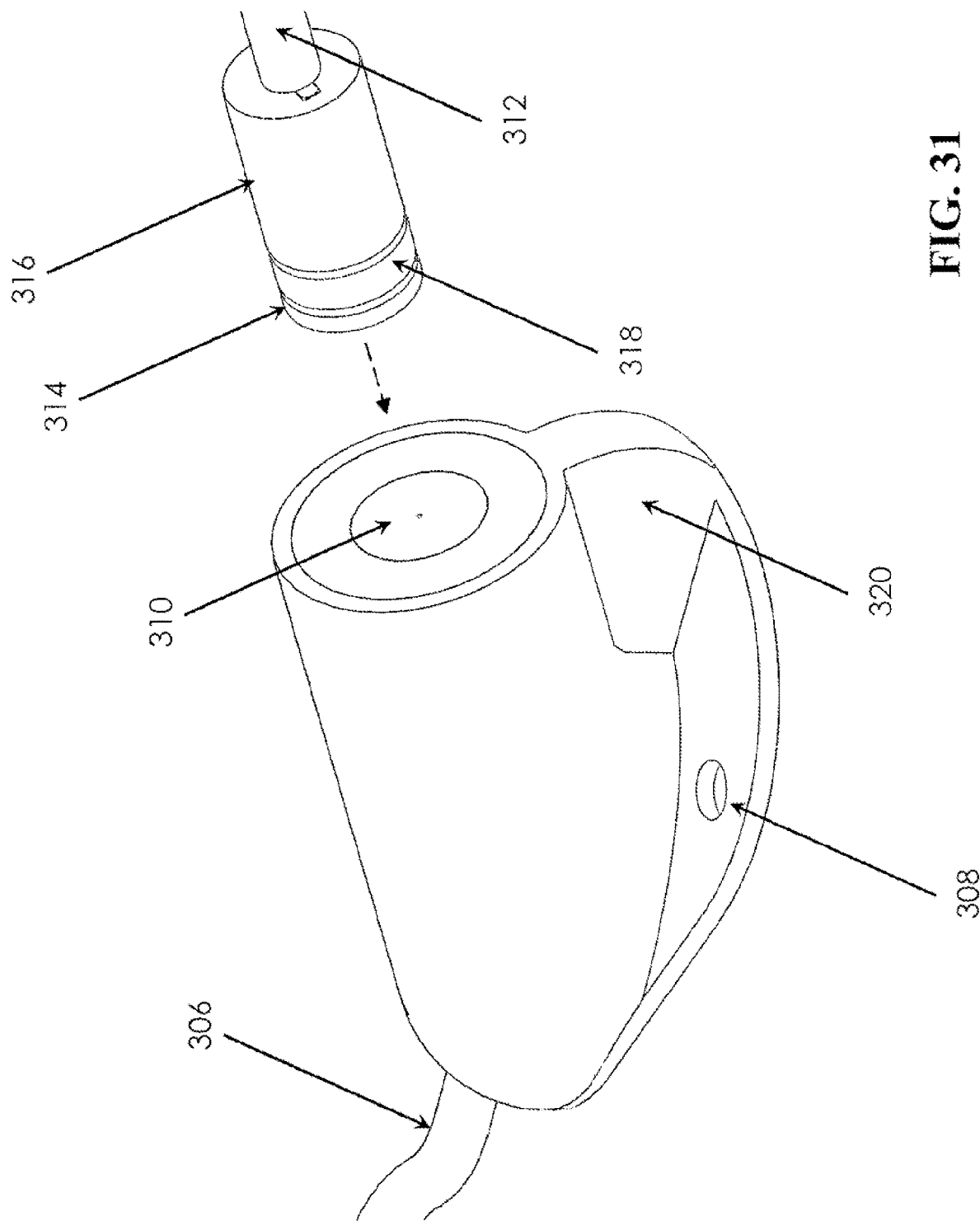
FIG. 31 illustrates a perspective view of a distal connector and extension fitting, according to an embodiment of the present invention.

FIG. 31 illustrates a perspective view of a distal connector and extension fitting, according to an embodiment of the present invention. The figure shows the first of three steps in the sequence of connecting the extension fitting to the distal catheter connector (recall FIG. 24). The implanted catheter 306 is anchored to the patient by either a securement device or sutures 308, as is common to the field. The septum 310 is sealed to prevent external contamination. The extension fitting 312 consists of an internal component 314 that follows a linear translation when connecting with the distal catheter connector, an external housing 316, and a flexible gasket 318.

Further with respect to FIG. 31, the distal catheter connector is angled away from the patient's skin to facilitate connecting the extension fitting. To prevent tangling, the outer housing may contain a rib 320.

Figure 32:
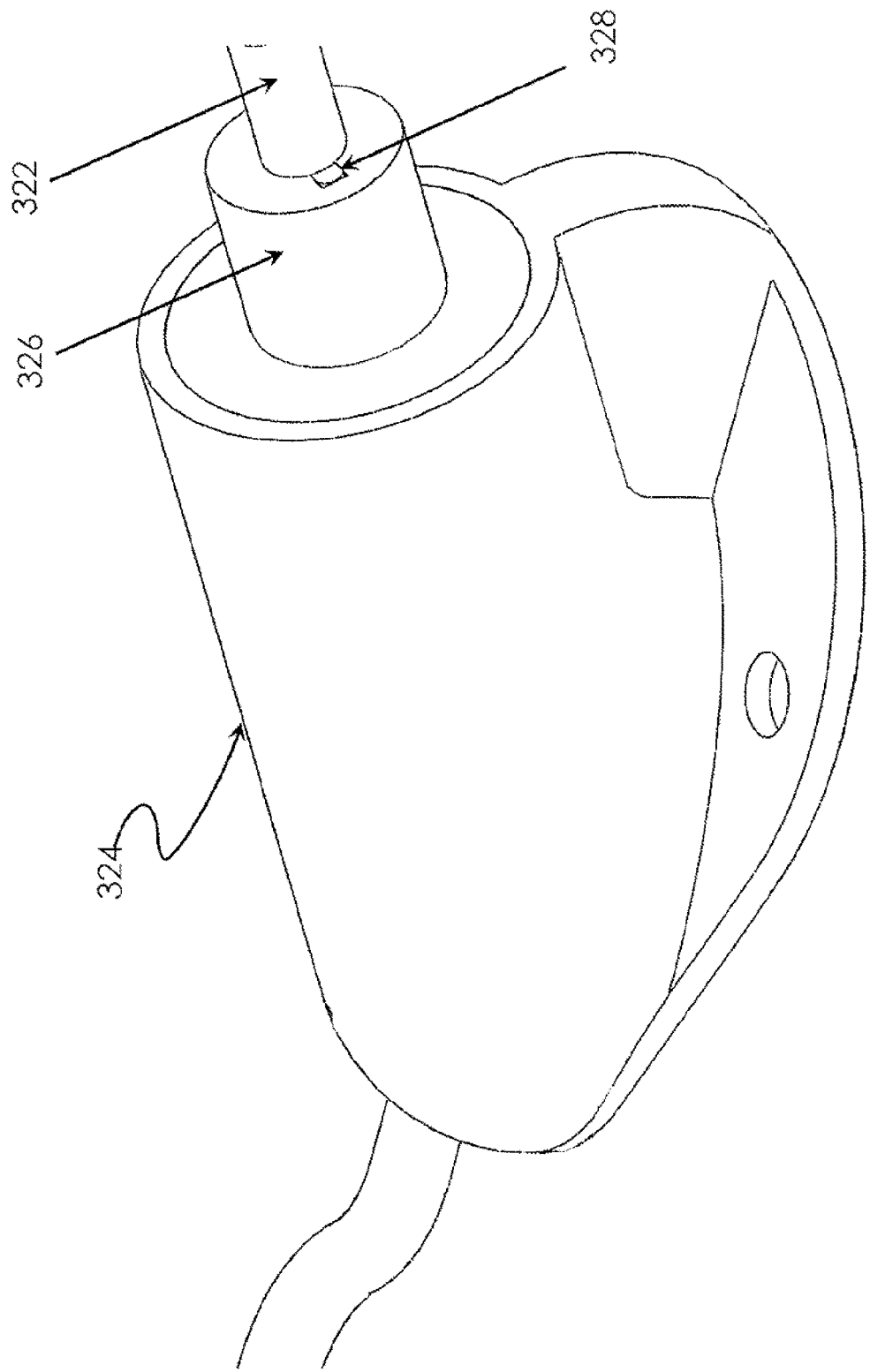
FIG. 32 illustrates a perspective view of a distal connector and extension fitting, according to an embodiment of the present invention.

FIG. 32 illustrates a perspective view of a distal connector and extension fitting, according to an embodiment of the present invention. The figure shows the second of three steps in the sequence of connecting the extension fitting to the distal catheter connector. The extension fitting 322 is seated against the internal cannula ledge (recall FIG. 25) of the distal catheter connector 324. The outer component 326 of the extension fitting remains displaced (by the inner spring of the extension fitting), as indicated by the tab 328 on the extension fitting.

Figure 33:
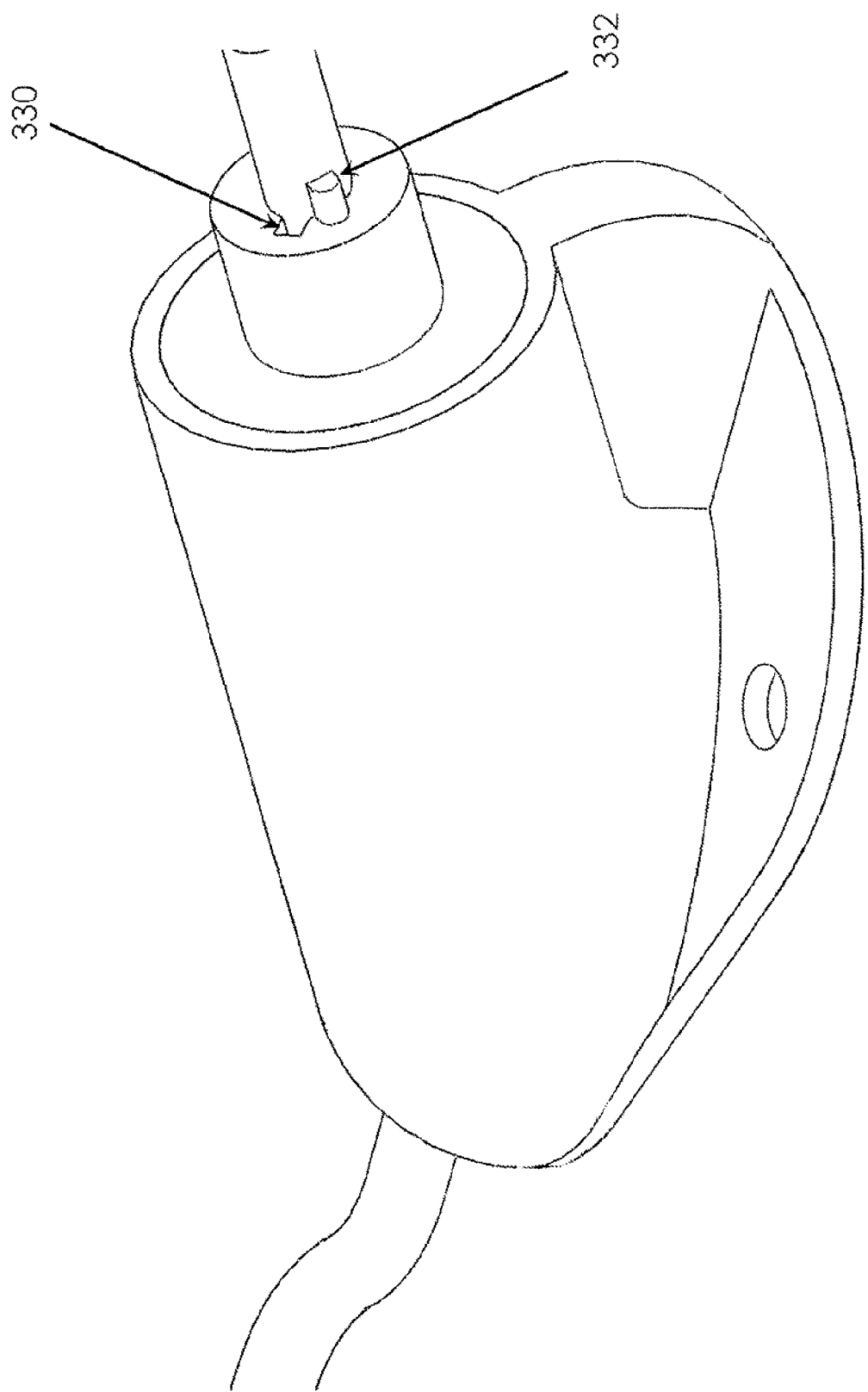
FIG. 33 illustrates a perspective view of a distal connector and extension fitting, according to an embodiment of the present invention.

FIG. 33 illustrates a perspective view of a distal connector and extension fitting, according to an embodiment of the present invention. The figure shows the final step in the three-step sequence of connecting the extension fitting to the distal catheter connector. The outer component of the extension fitting 330 advances further, compressing and expanding the flexible gasket on the extension fitting (recall FIG. 26). The outer component is temporarily locked in place by a small twisting action which is held in place by a tab 332 on the extension fitting. Alternative temporary locking mechanisms could include threads, friction fits, etc. The twisting of the outer component of the extension fitting does not create torsional forces on the inner portion which is engaged with one or more internal cannulas.

Figure 34:
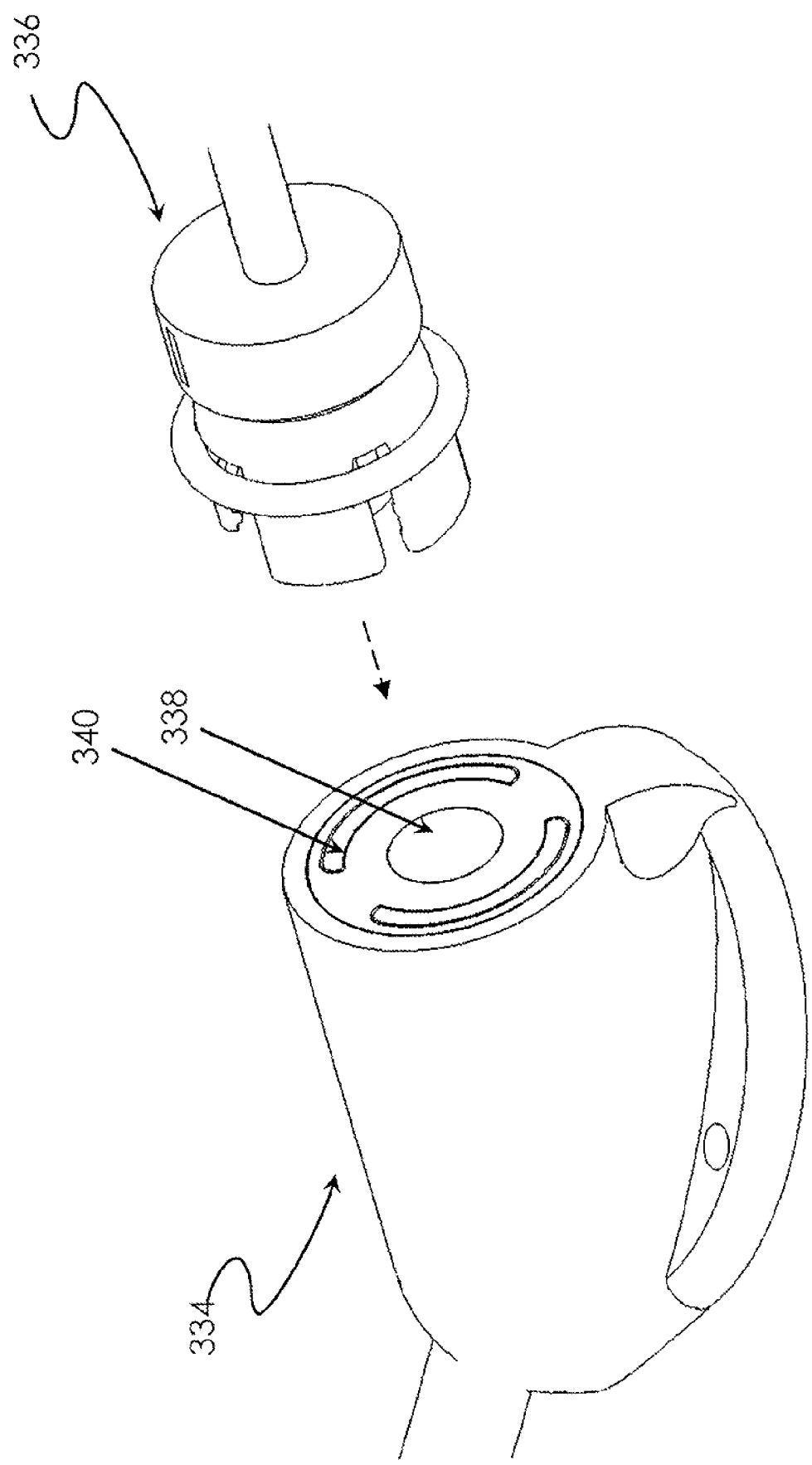
FIG. 34 illustrates a perspective view of a distal connector and extension fitting, according to an embodiment of the present invention.

FIG. 34 illustrates a perspective view of a distal connector and extension fitting, according to an embodiment of the present invention. The figure shows yet another embodiment of a distal catheter connector 334 and extension fitting 336 that engages in the absence of a rotational or twisting action. The catheter may be a single or multi-lumen catheter. The distal catheter connector contains a single septum 338 and a key-type fitting 340. The key-type fitting is sealed by a plastic member and displaced upon connecting the extension fitting. The member sealing the key-type fitting may be maintained by a spring or elastic mechanism (not shown).

Figure 35:
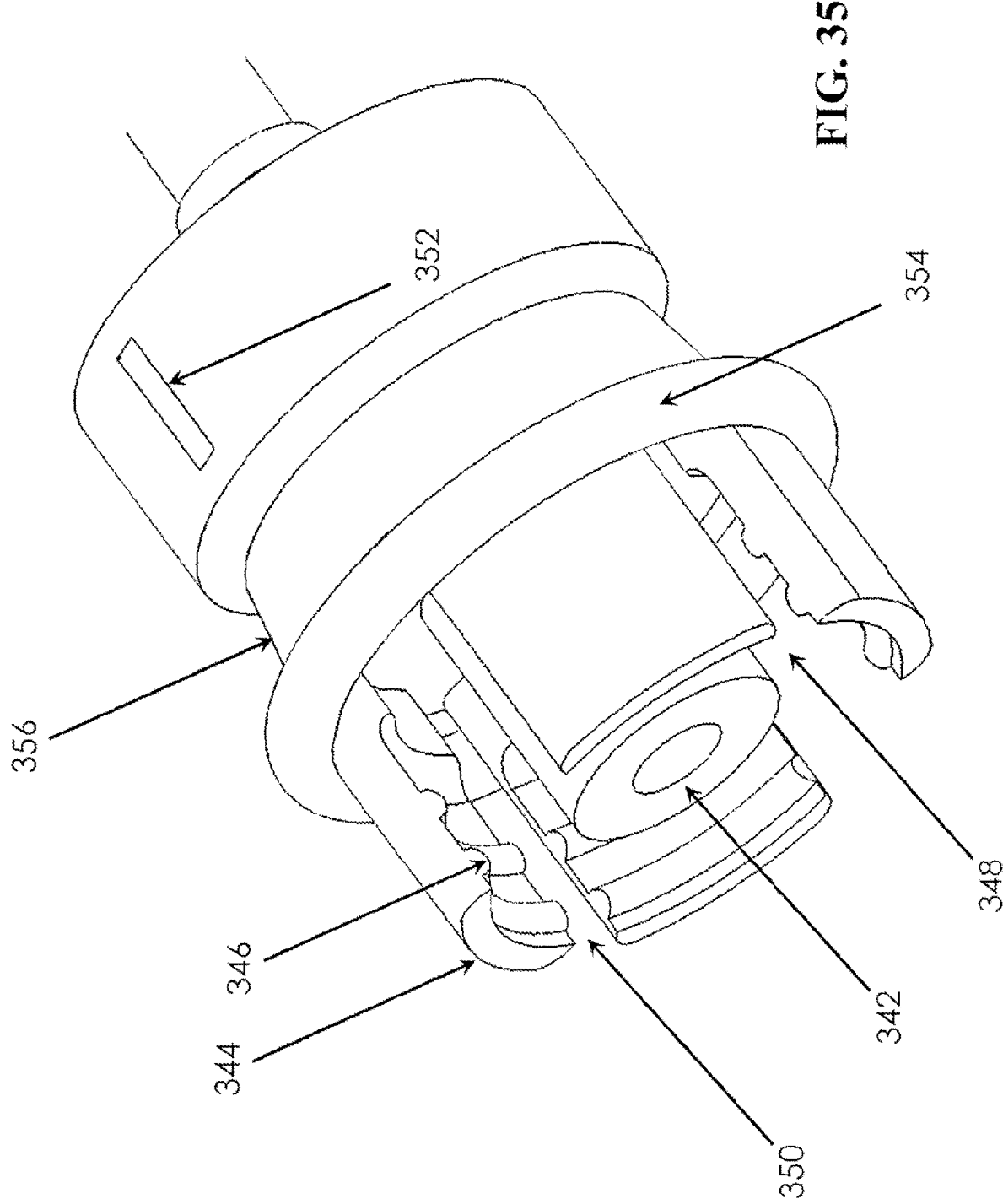
FIG. 35 illustrates a perspective view of an extension fitting, according to an embodiment of the present invention.

FIG. 35 illustrates a perspective view of an extension fitting, according to an embodiment of the present invention. The extension fitting is shown as a single lumen fitting 342 but may be multi-luminal. The fitting contains a series of tabs 344 with internal grooves 346 that decrease the inner diameter of the extension fitting. The tabs are shown with a large gap 348 and smaller gaps 350 to ensure one-way directionality (recall FIG. 34). The extension fitting may also contain a marking 352 to demonstrate to the user proper orientation of the fitting. The extension fitting uses an O-ring 354 that compresses the tabs 344 such that the inner grooves 346 lock against an internal ledge of the distal catheter connector. The smaller gaps 350 provide flexibility to the locking tabs such that they may be compressed. Above the O-ring is a tapered region 356. The extension fitting is shown in the attached state, where the O-ring compresses the tabs and locks the device to the distal catheter connector.

Figure 36:
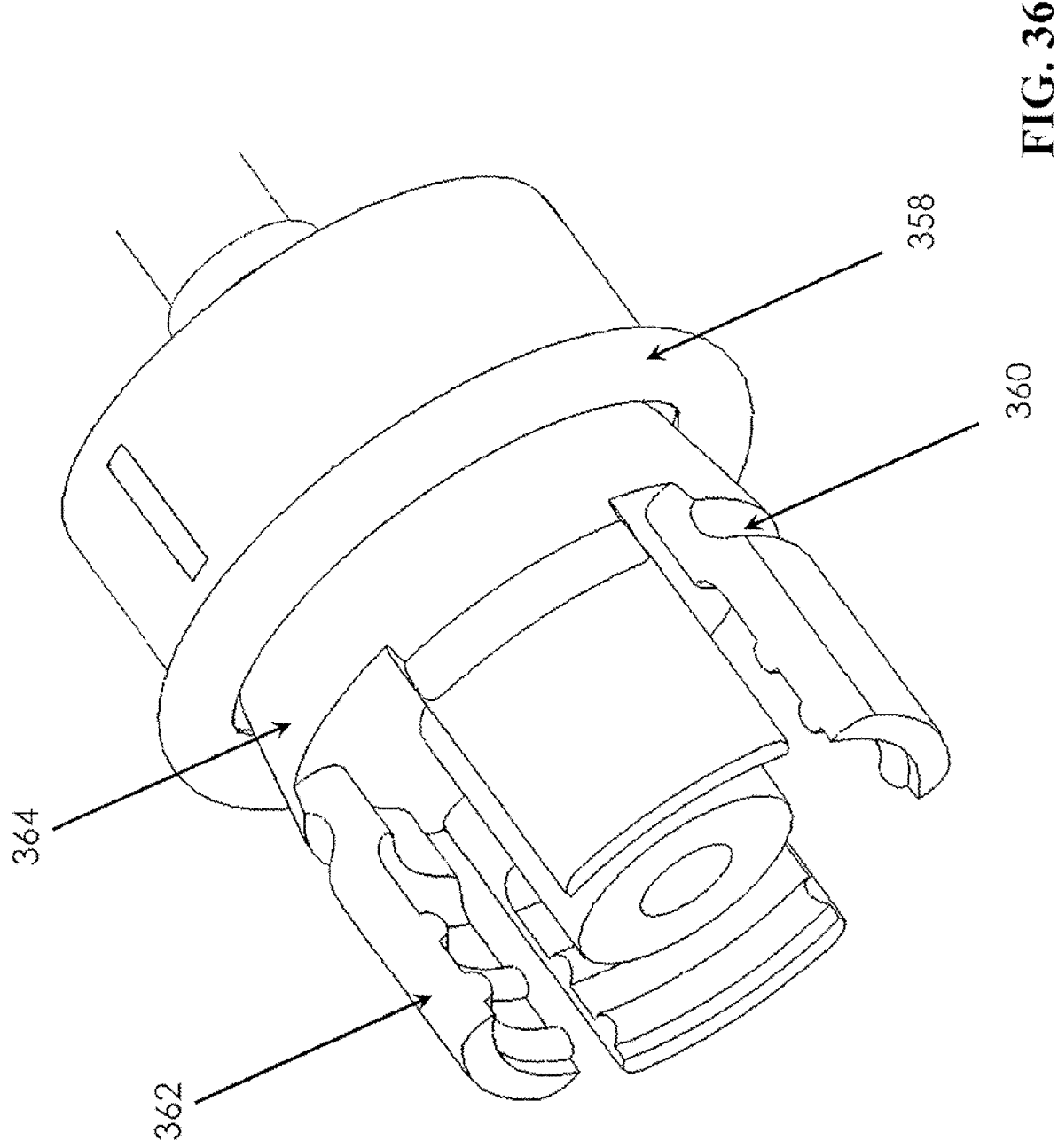
FIG. 36 illustrates a perspective view of an extension fitting, according to an embodiment of the present invention.

FIG. 36 illustrates a perspective view of an extension fitting, according to an embodiment of the present invention. The figure shows the detached state of the extension fitting, with respect to the distal catheter connector, in which the O-ring 358 has been removed from the groove 360 that compressed the locking tabs 362. The O-ring is moved down the tapered portion of the extensions fitting 364 to a region with a smaller inner diameter to release the locking tabs from the compressed state.

Figure 37:
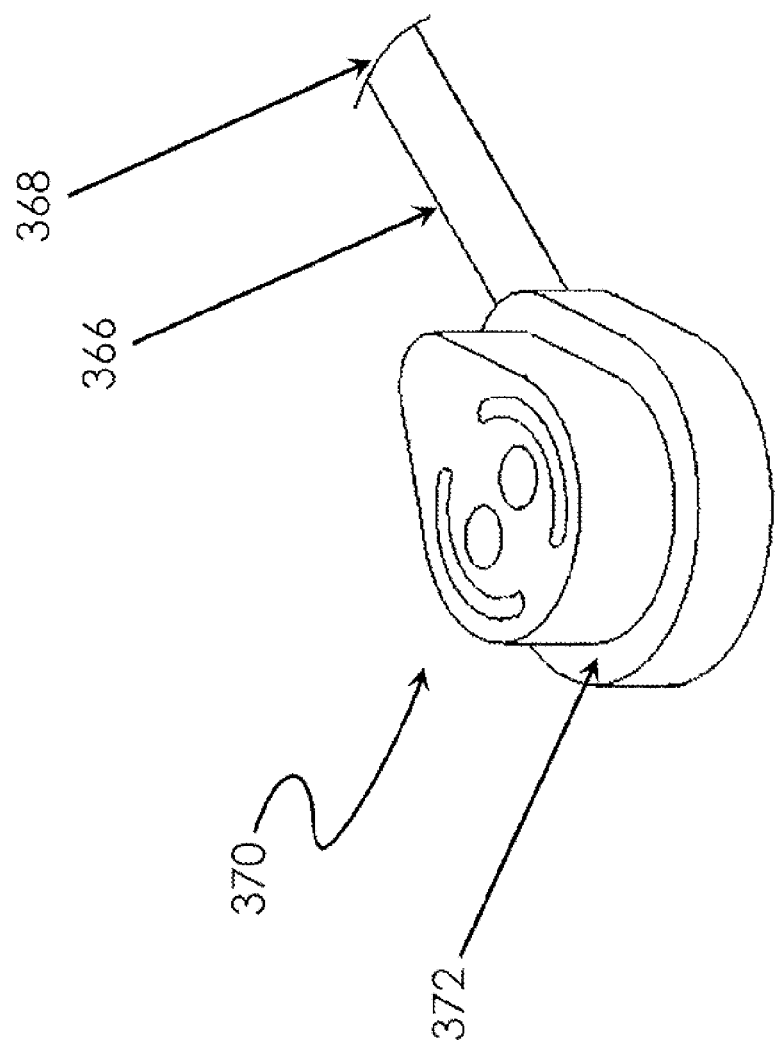
FIG. 37 illustrates a perspective view of an implanted catheter and distal connector, according to an embodiment of the present invention.

FIG. 37 illustrates a perspective view of an implanted catheter and distal connector, according to an embodiment of the present invention. The figure shows a multi-lumen catheter 366 that has been implanted in the patient 368. The distal catheter connector 370 contains a layered base 372 to facilitate application of a sterile dressing.

Figure 38:
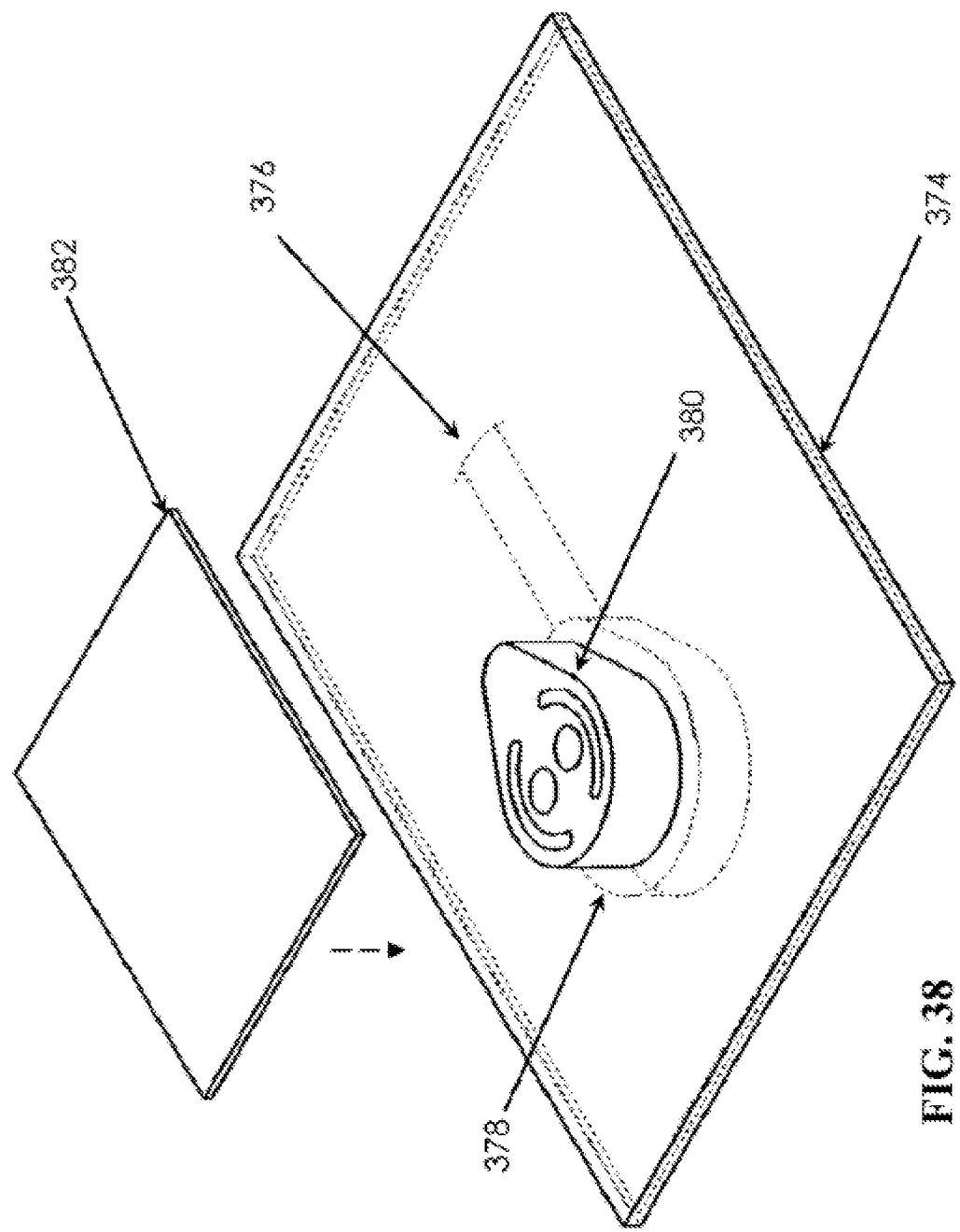
FIG. 38 illustrates a perspective view of an implanted catheter, distal connector, and insertion site dressing, according to an embodiment of the present invention.

FIG. 38 illustrates a perspective view of an implanted catheter, distal connector, and insertion site dressing, according to an embodiment of the present invention. The figure shows the application of a sterile dressing 374 that completely covers the insertion site and external catheter portion 376, with an opening in the dressing that covers a portion of the distal catheter connector 378, but keeps the portion of the connector that engages with a disposable extensions system 380 above the sterile dressing. A second bandage 382 may be added to cover the exposed portion of the distal catheter connector 380 and adhere to the top of the sterile dressing 374. In this way the entire system may be kept water-tight and helps keep the catheter clean. The second bandage 382 may be replaced during each catheter access while the sterile dressing below may be kept without needing replacement for longer periods of time.

Figure 39:
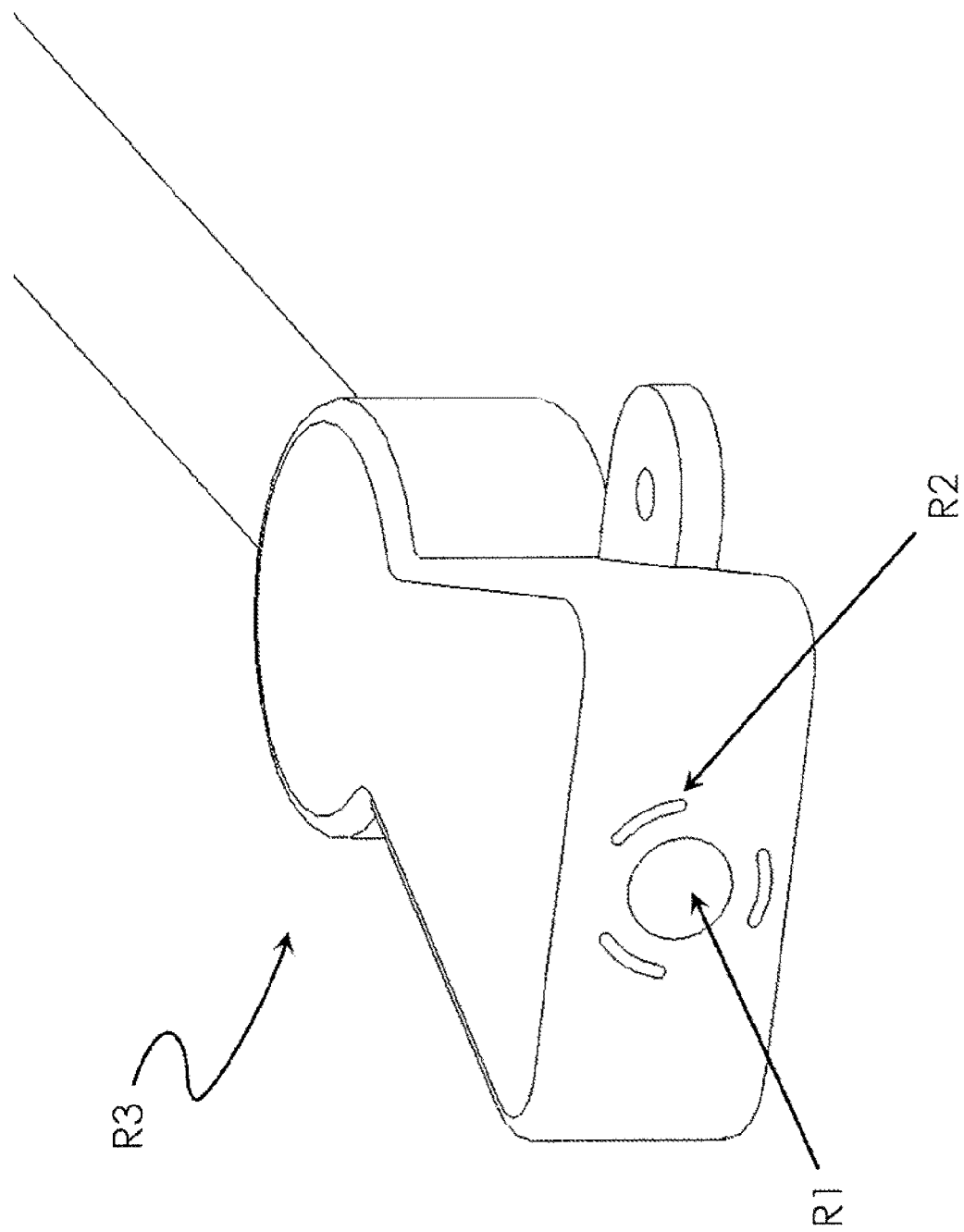
FIG. 39 illustrates a perspective view of a distal connector with a key-type connector, according to an embodiment of the present invention.

FIG. 39 illustrates a perspective view of a distal connector with a key-type connector, according to an embodiment of the present invention. The figure shows a distal catheter connector 384 with a key-type fitting 386 for a single lumen catheter 388.

Figure 40:
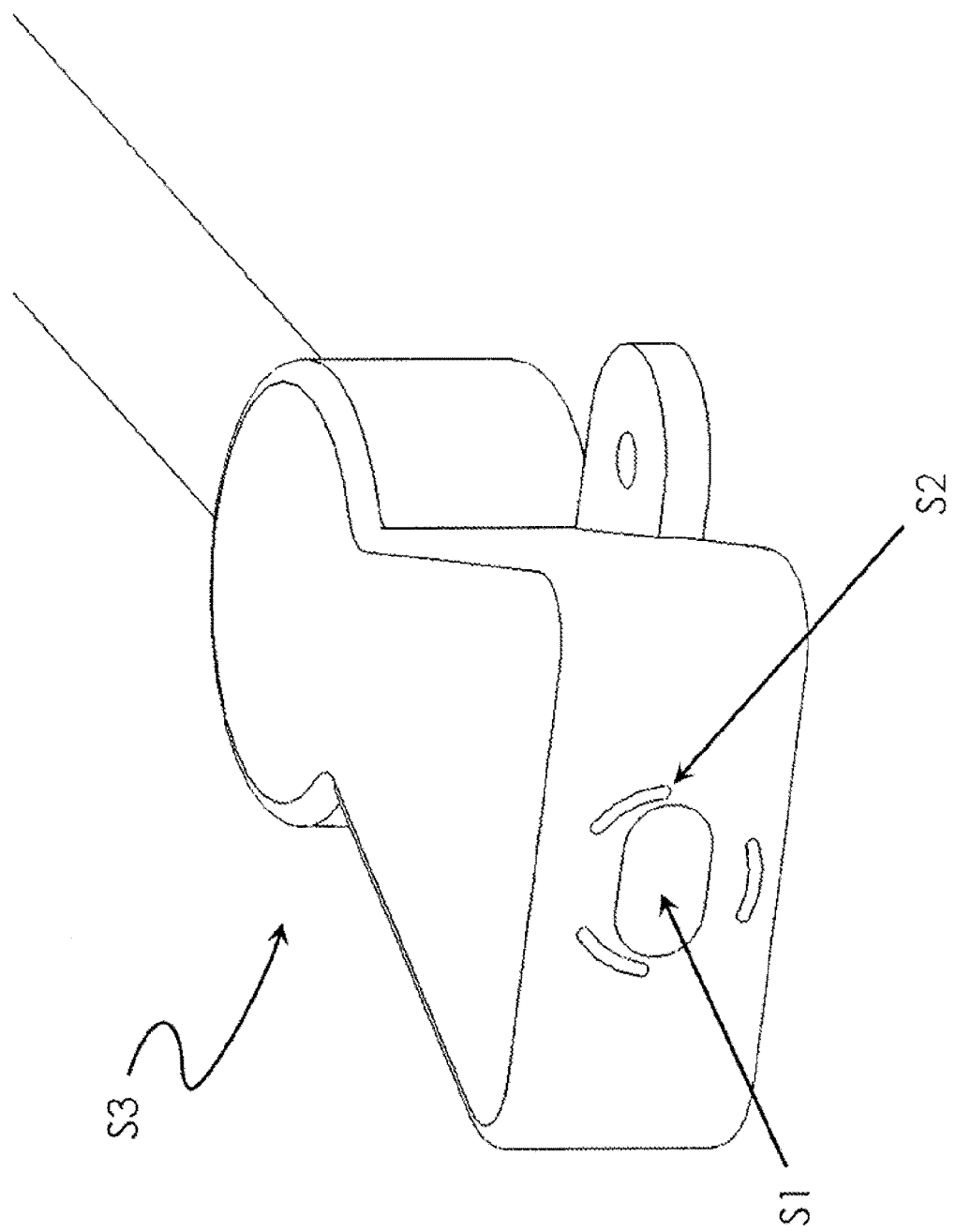
FIG. 40 illustrates a perspective view of a distal connector with a key-type connector, according to an embodiment of the present invention.

FIG. 40 illustrates a perspective view of a distal connector with a key-type connector, according to an embodiment of the present invention. The figure shows a distal catheter connector 390 with a key-type fitting 392 for a double lumen catheter 394. The shape combination ensures one-way polarity of the extension fitting.

Figure 41:
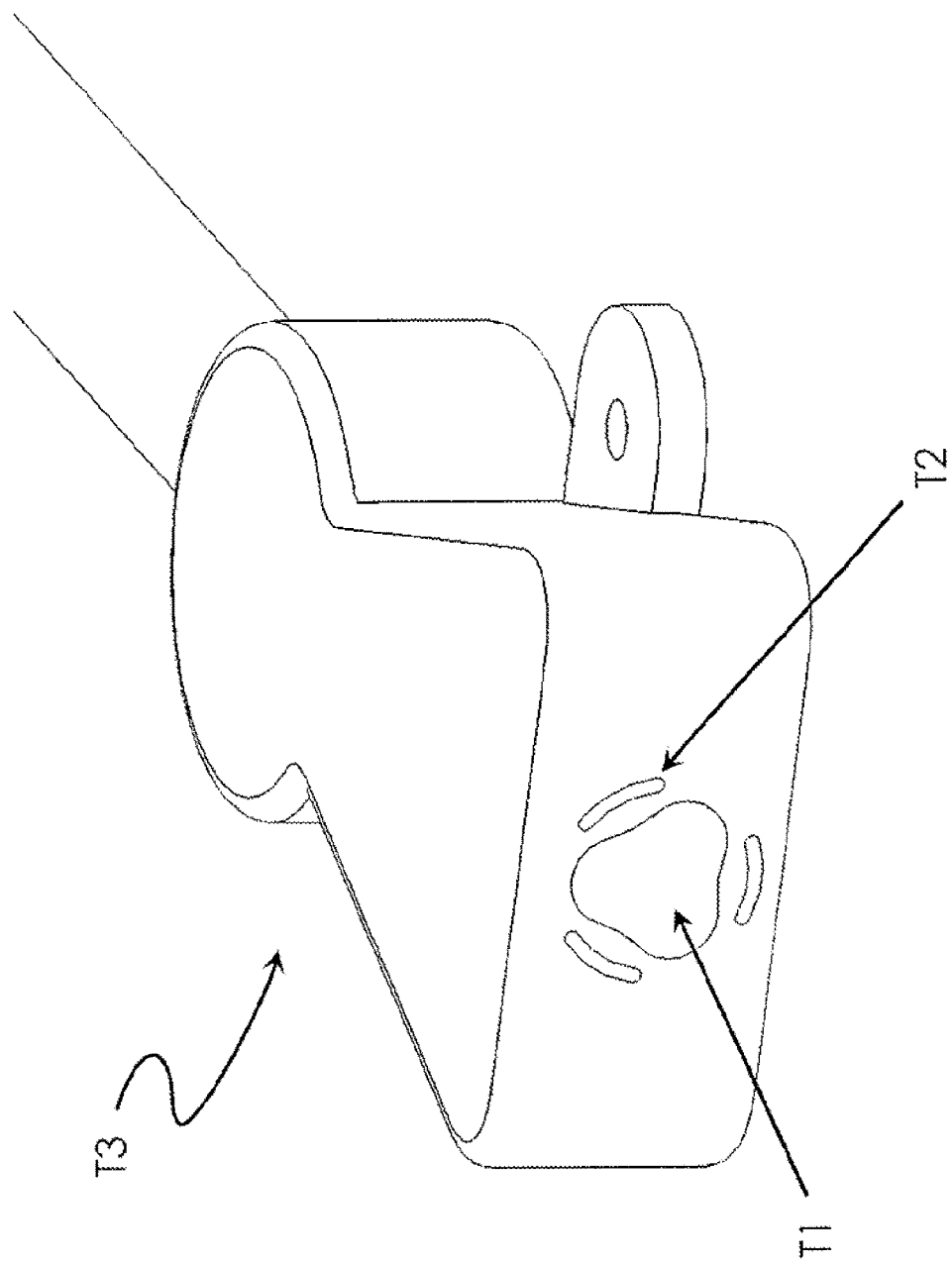
FIG. 41 illustrates a perspective view of a distal connector with a key-type connector, according to an embodiment of the present invention.

FIG. 41 illustrates a perspective view of a distal connector with a key-type connector, according to an embodiment of the present invention. The figure shows a distal catheter connector 396 with a key-type fitting 398 for a triple lumen catheter 400. The shape combination ensures one-way polarity of the extension fitting.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A catheter comprising:
   a hub having an outer housing defining a proximal end and a distal end, wherein the distal end of the outer housing defines an opening into an inner space defined by the outer housing, and disposed within the inner space is a distal connector, and wherein the proximal end of the housing defines a proximal connector for coupling to an intravenous catheter tube;
   a self-sealing septum disposed within the opening defined by the distal end of the outer housing, such that the self-sealing septum forms a barrier for the distal connector; and
   an extension tube assembly, wherein the extension tube assembly includes an extension tube and a locking key-type connector for coupling the extension tube to the distal connector through the self-sealing septum,
   wherein the extension tube assembly includes a luer that is separated into a plunger and a luer taper,
   wherein the plunger is formed integrally with the locking key-type connector and remains isolated from a fluid path, and
   wherein the plunger extends further than the luer taper to engage with and displace the self-sealing septum.

2. The catheter of claim 1 further comprising a locking key-type cover for covering the opening and the septum when the catheter is not in use.

3. The catheter of claim 2 wherein the locking key-type cover further comprises plugged luer channels.

4. The catheter of claim 1 wherein the extension tube further comprises a number of extension tubes in a range of 1-4 extension tubes.

5. The catheter of claim 1 wherein the self-sealing septum further comprises slits in order to allow the connection of the extension tube assembly.

6. The catheter of claim 1 wherein the plunger comprises threading.

7. The catheter of claim 1 wherein the self-sealing septum is reset using a slider or elastic band mechanism.

8. The catheter of claim 1 further comprising an integrated catheter connector with a septum and a clamp.

9. The catheter of claim 1 further comprising a secondary clamp that enables replacement of the extension tube assembly.

10. The catheter of claim 1 wherein the intravenous catheter tube includes a single lumen or multiple lumens.

\* \* \* \* \*